(12) United States Patent
Possemiers et al.

(10) Patent No.: US 11,633,440 B2
(45) Date of Patent: *Apr. 25, 2023

(54) USE OF MICROBIAL COMMUNITIES FOR HUMAN AND ANIMAL HEALTH

(71) Applicants: Universiteit Gent, Ghent (BE); Microbial Resource Management Health NV (MRM Health), Ghent (BE)

(72) Inventors: Sam Possemiers, Zwijnaarde (BE); Massimo Marzorati, Brussels (BE); Tom Van De Wiele, Merelbeke (BE); Ilse Scheirlinck, Gentbrugge (BE); Pieter Van Den Abeele, Lokeren (BE); Selin Bolca, Zwijnaarde (BE); Davide Gottardi, Ghent (BE)

(73) Assignees: Microbial Resource Management Health NV (MRM Health); Universiteit Gent

( * ) Notice: Subject to any disclaimer, the term of this patent is extended or adjusted under 35 U.S.C. 154(b) by 0 days.

This patent is subject to a terminal disclaimer.

(21) Appl. No.: 17/937,553

(22) Filed: Oct. 3, 2022

(65) Prior Publication Data

US 2023/0045069 A1    Feb. 9, 2023

Related U.S. Application Data

(63) Continuation of application No. 17/502,445, filed on Oct. 15, 2021, now Pat. No. 11,491,196, which is a continuation of application No. 17/386,266, filed on Jul. 27, 2021, which is a continuation of application No. 16/068,470, filed as application No. PCT/EP2017/052422 on Feb. 3, 2017, now Pat. No. 11,096,971.

(30) Foreign Application Priority Data

Feb. 4, 2016 (EP) .................................... 16154288

(51) Int. Cl.

| A61K 9/00 | (2006.01) |
| A61K 35/747 | (2015.01) |
| A23L 33/135 | (2016.01) |
| C12N 1/20 | (2006.01) |
| A61K 35/741 | (2015.01) |
| A61P 1/14 | (2006.01) |
| A61K 35/74 | (2015.01) |
| A61K 35/744 | (2015.01) |
| A61K 35/745 | (2015.01) |
| A61K 35/00 | (2006.01) |

(52) U.S. Cl.
CPC .......... *A61K 35/747* (2013.01); *A23L 33/135* (2016.08); *A61K 9/0031* (2013.01); *A61K 9/0053* (2013.01); *A61K 9/0056* (2013.01); *A61K 35/74* (2013.01); *A61K 35/741* (2013.01); *A61K 35/744* (2013.01); *A61K 35/745* (2013.01); *A61P 1/14* (2018.01); *C12N 1/20* (2013.01); *A23V 2002/00* (2013.01); *A23Y 2220/67* (2013.01); *A23Y 2300/19* (2013.01); *A23Y 2300/55* (2013.01); *A61K 2035/115* (2013.01); *Y02A 50/30* (2018.01)

(58) Field of Classification Search
CPC .. A61K 35/747; A61K 9/0031; A61K 9/0053; A61K 9/0056; A61K 35/74; A61K 35/741; A61K 35/744; A61K 35/745; A61K 2035/115; A23L 33/135; A61P 1/14; C12N 1/20; A23Y 2220/67; A23Y 2300/19; A23Y 2300/55; Y02A 50/30
See application file for complete search history.

(56) References Cited

U.S. PATENT DOCUMENTS

| 2007/0258953 A1 | 11/2007 | Duncan |
| 2008/0311097 A1 | 12/2008 | Israelsen |
| 2011/0189147 A1 | 8/2011 | Garner |
| 2012/0027734 A1 | 2/2012 | Van Immerseel |
| 2012/0034198 A1 | 2/2012 | Garner |
| 2014/0199281 A1 | 7/2014 | Henn |
| 2014/0227227 A1 | 8/2014 | Junjie |
| 2015/0132264 A1 | 5/2015 | Kelly |
| 2016/0228476 A1 | 8/2016 | Cutcliffe |
| 2017/0260552 A1 | 9/2017 | Haas |

FOREIGN PATENT DOCUMENTS

| CN | 101353633 B | 12/2011 |
| KR | 20150108357 A | 9/2015 |
| WO | 2007036230 | 4/2007 |
| WO | 2012142605 A1 | 10/2012 |
| WO | 2013037068 | 3/2013 |
| WO | 2014075745 A1 | 5/2014 |
| WO | 2014137211 | 9/2014 |

(Continued)

OTHER PUBLICATIONS

Li, X., et al., "Complete genome sequence of the probiotic Lactobacillus plantarum strain ZJ316" Genome Announc. Mar. 21, 2013;1(2):e0009413. doi: 10.1128/genomeA.00094-13.

(Continued)

*Primary Examiner* — Satyendra K Singh
(74) *Attorney, Agent, or Firm* — Greenberg Traurig, LLP

(57) ABSTRACT

The disclosure relates to a mixture of bacteria belonging to at least six or seven different and specific bacterial species preferably for use in preventing or treating gastro-intestinal disorders. Preferably, the mixture of bacteria is grown together in a fermenter prior to administering the mixture to a subject in order to prevent or treat the disorder.

22 Claims, 12 Drawing Sheets

Specification includes a Sequence Listing.

(56) References Cited

FOREIGN PATENT DOCUMENTS

| | | |
|---|---|---|
| WO | 2014145958 | 9/2014 |
| WO | 2017134240 | 8/2017 |

OTHER PUBLICATIONS

Altschul, S.F., et al., Basic Local Alignment Search Tool, J. Mol. Biol (1990) 215,403-410.
Bahka, D. et al., "Phenotypic and Genomic Analyses of Human Strains Belonging or Related to Bifidobacterium longum, Bifidobacterium infantis, and Bifidobacterium breve", International Journal of Systematic Bacteriology, Jul. 1993, pp. 565-573.
Barcenilla, A. et al., "Phylogentic Relationships of Butyrate-Producing Bacteria from the Human Gut" Applied and Environmental Microbiology, Apr. 2000, p. 1654-1661.
Barnett, A.M., et al., "The Interactions between Engogenous Bacteria, Dietary Components and the Mucus Layer of the Large Bowel" Food Funct., 2012, 3, 690-699.
Boon, N., et al., "Bioaugmentation as a Tool To Protect the Structure and Function of an Activated-Sludge Micorbial Community against a 3-Chloroaniline Shock Load", Applied and Environmental Microbiology, Mar. 2003, pp. 1511-152.
Brandl, K., et al., "Vancomycin-Resistant Enterococci Antibiotic-Inducted Innate Immune Deficits", Nature, 2008, 455 (7214): 804-807.
Cenit, M.C., et al., "Rapidly Expanding Knowledge on the Role of the Gut Microbiome in Health and Disease" Biochim Biophys Acta 1842:1984-1992.
Clemente, J.C., et al., "The Impact of the Gut Microbiota on Human Health: An Integrative View", Cell, 2012; 148(6):1258-1270.
Deboever, P., et al., "Fermentation by Gut Microbiota Cultured in a Simulator of the Human Intestinal Microbial Ecosystem is Improved by Supplementing a Soygerm Powder", 2000, The Journal of Nutrition, 130(10):2599-2606.
DSM 23266 (LMG-24109), Butyricicoccus pullicaecorum, DSMZ German Collection of Microorganisms and Cell Cultures, 2008 (Year: 2008).
DSM-14662, Anaerostipes caccae, DSMZ German Collection of Microorganisms and Cell Cultures, 2002 (Year: 2002).
DSM-16839, Roseburia hominis, DSMZ German Collection of Microorganisms and Cell Cultures, 2006 (Year: 2006).
DSM-16841, Roseburia inulinivorans, DSMZ German Collection of Microorganisms and Cell Cultures, 2006 (Year: 2006).
DSM-17677,Faecalibacterium prausnitzii, DSMZ German Collection of Micoorganisms and Cell Cultures, 2002, (Year: 2002).
DSM22959 , Akkermansia muciniphila, German Collection of Microorganisms and Cell culture, 2020.
DSM-22959, Akkermansia muciniphila, DSMZ German Collection of Microorganisms and Cell Cultures, 2004 (Year: 2004).
European Examination Report for EP Application No. 19212983 dated Feb. 12, 2021.
European Search Report for EP Application No. 19212983.1 dated Feb. 19, 2020.
Everard, A., et al., Cross-talk between Akkermansia muciniphila and intestinal epithelium controls diet-induced obesity, PNAS, May 2013, vol. 110, No. 22, pp. 9066-9071 (Year: 2013).
Geirnaert, A., et al., "Butyricicoccus pullicaecorum, a Butyrate Producer with Probiotic Potential, is Intrinsically Tolerant to Stomach and Small Intestine Conditions", Anaerobe. Dec. 2014;30:70-74.
Hartemink, R. et al., "Raffinose-Bifidobacterium (RB) Agar, a New Selective Medium for Bifidobacteria", J Microbiol. Methods 27 (1996) 33-43.
Hartemink, R., et al. (1997). "LAMVAB—A new selective medium for isolation of lactobacilli from faeces" pp. 127-138 In: "Prebiotic Effects of Non-Digestible Oligo-and Polysaccharides" Journal of Microbiological Methods, 29, 77-84.
Jannitti, T., et al., "Therapeutical Use of Probiotic Formulations in Clinical Practice", Clinical Nutrition 29 (2010) pp. 701-725.
International Search Report for PCT/EP2017/05422 dated Jun. 2, 2017.
Keefe, D. M. K., "Gastrointestinal Mucositis: a New Biological Model", Suport Care Cancer, (2004) 12(1)"6-9.
Kinross, J.M., et al., "Gut Microbiome-Host Interactions in Health and Disease", Genome Medicine, (2011)3:14.
Le Bon, M., et al., "Influence of Probiotics on Gut Health in the Weaned Pig", Livestock Science 133 (2010) 179-181.
Livingston, S.J., et al., "New Medium for Selection and Presumptive Identification of the Bacteroides fragilis Group", J Clin Microbiol. (1978) pp. 448-453.
Machiels, K., et al. "A Decrease of The Butyrate-Producing Speciesroseburia Hominisandfaecalibacterium Prausnitziidefines Dysbiosis In Patients With Ulcerative Colitis", 2013, Gut, vol. 63, No. 8, pp. 1275-1283.
Newton, D.F., et al., "Growth of a Human Intestinal Desulfovibrio desulfuricans in Continuous Cultures Containing Defined Populations of Saccharolytic and Amino Acid Fermenting Bacteria", Journal of Applied Microbiol. (1998) 85:372-380.
Panda, S., et al., "Short-Term Effect of Antibiotics on Human Gut Microbiota", 2014 PLoS ONE 9(4):e95476.
Petrof, E.O., et al., "Stool Substitute Transplant Therapy for the Eradication of Clostridium difficile infection: RePoopulating' the Gut", Microbiome 2013, 1:3.
Possemiers, S., et al., "PCR-DGGE-based Quantification of Stability of the Microbial Community in a Simulator of the Human Intestinal Microbial Ecosystem", FEMS Microbiology Ecology (2004) 49:495-507.
Scharek, L., et al., "Bifidobacterium Adolescentis Modulates the Specific Immune Response to Another Human Gut Bacterium, Bacteroides thetaiotaomicros, in Gnotobiotic Rats", Immunobiology (2002) 202:429-441.
Scheiffele, F., et al., "Induction of TNBS colitits in Mice", Curr Protocols Immunol (2001) 15.19.1-15.19.14.
Schleifer, K.H., et al., "Transfer of *Streptococcus faecalis* and *Streptococcus faecium* to the Genus *Enterococcus* nom. rev. as *Enterococcus faecalis* comb. nov. and *Enterococcus faecium* comb. nov." International J Systematic Bacteriology, Jan. 1984, pp. 31-34.
Schwiertz, A., et al. "*Anaerostipes caccae* gen. nov., a New Saccharolytic Acetate-utilizing, Butyrate-producing Bacterium from Human Faeces", System Appl. Microbiol. 25:46-51 (2002).
Scott, K.P., et al., "Manipulating the Gut Microbiota to Maintain Health and Treat Disease", Microbial Ecology in Health and Disease 26:1-10 (2015).
Seikrov, I., et al., "Antibiotic-Induced Perturbations of the Intestinal Microbiota Alter Host Susceptibility to Enteric Infection", Infection and Immunity (2008) pp. 4726-4736.
Sokol, H., et al., Faecalibacterium prausnitzii is an anti-inflammatory commensal bacterium identified by gut microbiota analysis of Crohn disease patients, PNAS, vol. 105, No. 43, Oct. 2008, 16731-16736 (2008).
Thomas, L.V., "Exploring the Influence of the Gut Microbiota and Probiotics on Health: a Symposium Report", British Journal of Nutrition, 112(s1):S1-S18 (2014).
Van De Wiele, T., et al., "The Simulator of the Human Intestinal Microbial Ecosystem (SHIME®)" Chapter 27 In: "The Impact of Food Bioactives on Health", 2015, Springer International Publishing, Cham (2015).
Van Den Abbeele, P., et al., "Microbial Community Development in a Dynamic Gut Model is Reproducible, Colon Region Specific and Selective for Bacteroidetes and Clostridium Cluster IX #", Applied and Environmental Microbiology 76(15):5237-5246 (2010).
Van Den Abbeele, P., et al., "Prebiotics, faecal Transplants and Microbial Network Units to Stimulate Biodiversity of the Human Gut Microbiome", Microbial Biotechnology 6(4):335-340 (2013).
Van Loo, J., et al., "Functional Food Properties of Non-Digestible Oligosaccharides: A Consensus Report from the ENDO Project (DGXII AIRII-CT94-1095)" British Journal of Nutrition 81:121-132 (1999).
Venegas, et al., "SCFA-Mediated Gut Epithelial and Immune Regulation and its Relevance for Inflammatory Bowel Disease", Frontier in Immunology, Mar. 2019, vol. 10, article 277.

(56) References Cited

OTHER PUBLICATIONS

Vermeiren, J., et al., "Decreaded Colonization of fecal Clostridium coccoides/Eubacterium Rectal Species from Ulcerative colitis Patients in an in vitro Dynamic Gut Model with Mucin Environment", FEMS Microbiol Ecol 79:685-696 (2012).

Vignaes, L.K., et al., "Microbiotas from UC Patients Display Altered Metabolism and Reduced Ability of LAB to colonize Mucus", Sci Rep. 2013;3:1110. doi:10.1038/srep01110.

Walter, J., "Ecological role of lactobacilli in the gastrointestinal tract: implications for fundamental and biomedical research", Appl Environ Microbiol. 2008;74(16):4985-4996.

Weisburg, W.G., et al., "16S Ribosomal DMA Amplification for Phylogenetic Study", Journal of Bacteriology, 173(2):697-703 (1991).

Willing, B., et al., "Twin Studies Reveal Specific Imbalances in the Mucosa-associated Microbiota of Patients with Ileal Crohns Disease" Inflamm Bowel Dis 15(5):653-600 (2009).

Zampa, A., et al., "Effects of different digestible carbohydrates on bile acid metabolism and SCFA production by human gut microflora grown in an in vitro semi-continuous culture" Anaerobe. Feb. 2004;10(1):19-26.

SEQUENCE LISTING

```
Sequence total quantity: 9
SEQ ID NO: 1            moltype = DNA   length = 1485
FEATURE                 Location/Qualifiers
source                  1..1485
                        mol_type = genomic DNA
                        organism = Roseburia hominis
SEQUENCE: 1
gatcctggct caggatgaac gctggcggcg tgcttaacac atgcaagtcg aacgaagcac   60
tttaattgat ttcttcggaa tgaagttttt gtgactgagt ggcggacggg tgagtaacgc   120
gtgggtaacc tgcctcatac aggggataa cagttggaaa cgactgctaa taccgcataa    180
gcgcacagga ttgcatgatc cagtgtgaaa aactccggtg gtatgagatg gacccgcgtc   240
tgattagcca gttggcgggg taacggccca ccaaagcgac gatcagtagc cgacctgaga   300
gggtgaccgg ccacattggg actgagacac ggcccaaact cctacgggag gcagcagtgg   360
ggaatattgc acaatggggg aaaccctgat gcagcgacgc cgcgtgagcg aagaagtatt   420
tcggtatgta aagctctatc agcagggaag aagaatgcgg tacctgacta agaagcaccg   480
gctaaatacg tgccagcagc cgcggtaata cgtatgtgc aagcgttatc cggatttact    540
gggtgtaaag ggagcgcagg cggtacggca agtctgatgt gaaatcccgg ggctcaaccc   600
cggtactgca ttggaaactg tcggactaga gtgtcggagg ggtaagtgga attcctagtg   660
tagcggtgaa atgcgtagat attaggagga acaccagtgg cgaaggcggc ttactggacg   720
attactgacg ctgaggctcg aaagcgtggg gagcaaacag gattagatac cctggtagtc   780
cacgccgtaa acgatgaata ctaggtgtcg gggagcattg ctcttcggtg ccgcagcaaa   840
cgcaataagt attccacctg gggagtacgt tcgcaagaat gaaactcaaa ggaattgacg   900
gggacccgca caagcggtgg agcatgtggt ttaattcgaa gcaacgcgaa gaaccttacc   960
aagtcttgac atcccactga cagagtatgt aatgtactt ctcttcggag cagtggtgac    1020
aggtggtgca tggttgtcgt cagctcgtgt cgtgagatgt tgggttaagt cccgcaacga   1080
gcgcaacccc tattcttagt agccagcggt tcggccggc actctaggga gactgccagg    1140
gataacctgg aggaaggtgg ggatgacgtc aaatcatcat gccccttatg acttgggcta   1200
cacacgtgct acaatggcgt aaacaagggg aagcaatccc gcgaggggga gcaaatctca   1260
aaaataacgt ctcagttcgg actgtagtct gcaactcgac tacacgaagc tggaatcgct   1320
agtaatcgcg aatcagaatg tcgcggtgaa tacgttcccg ggtcttgtac acaccgcccg   1380
```

```
tcacaccatg ggagttggta atgcccgaag tcagtgaccc aaccgcaagg agggagctgc    1440
cgaaggcagg actgataact ggggtgaagt cgtaacaagg gtacg                    1485

SEQ ID NO: 2             moltype = DNA   length = 1454
FEATURE                  Location/Qualifiers
source                   1..1454
                         mol_type = genomic DNA
                         organism = Roseburia inulinivorans
SEQUENCE: 2
ttgatcctgg ctcaggatga acgctggcgg cgtgcttaac acatgcaagt cgaacgaagc      60
acttttacag atttcttcgg aatgaagttt tagtgactga gtggcggacg ggtgagtaac     120
gcgtgggtaa cctgcctcac acaggggat  aacagttgga aacggctgct aataccgcat     180
aagcgcacag taccgcatgg tacagtgtga aaaactccgg tggtgtgaga tggacccgcg     240
tctgattagc tagttggcag ggtaacggcc taccaaggcg acgatcagta gccgacctga     300
gagggtgacc ggccacattg ggactgagac acgcccaaa  ctcctacggg aggcagcagt     360
ggggaatatt gcacaatggg ggaaaccctg atgcagcgac gccgcgtgag cgaagaagta     420
tttcggtatg taaagctcta tcagcaggga agaagaaatg acggtacctg actaagaagc     480
accggctaaa tacgtgccag cagccgcggt aatacgtag gtgcaagcgt tatccggatt     540
tactgggtgt aaagggagcg caggcggaag gctaagtctg atgtgaaagc ccggggctca     600
accccggtac tgcattggaa actggtcatc tagagtgtcg gaggggtaag tggaattcct     660
agtgtagcgg tgaaatgcgt agatattagg aggaacacca gtggcgaagg cggcttactg     720
gacgataact gacgctgagg ctcgaaagcg tggggagcaa acaggattag ataccctggt     780
agtccacgcc gtaaacgatg aatactaggt gtcggaaagc acagctttt  ggtgccgccg     840
caaacgcatt aagtattcca cctggggagt acgttcgcaa gaatgaaact caaaggaatt     900
gacgggaccc cgcacaagcg gtggagcatg tggtttaatt cgaagcaacg cgaagaacct     960
taccaagtct tgacatcctt ctgaccggac agtaatgtgt cctttccttc gggacagaag    1020
tgacaggtgg tgcatggttg tcgtcagctc gtgtcgtgag atgttgggtt aagtcccgca    1080
acgagcgcaa cccttatccc cagtagccag cggttcggac gggcactctg aggagactgc    1140
cagggataac ctggaggaag tggggatga cgtcaaatca tcatgcccct tatgacttgg    1200
gctacacacg tgctacaatg gcgtaaacaa agggaagcga ccgtgagg  tggagcaaat    1260
cccaaaaata acgtctcagt tcggactgta gtctgcaacc cgactacacg aagctggaat    1320
cgctagtaat cgcagatcag aatgctgcgg tgaatacgtt cccgggtctt gtacacaccg    1380
cccgtcacac catgggagtt ggaaatgccc gaagtcagtg acccaaccgc aaggagggag    1440
ctgcgaaggc aggt                                                     1454

SEQ ID NO: 3             moltype = DNA   length = 1433
FEATURE                  Location/Qualifiers
source                   1..1433
                         mol_type = genomic DNA
                         organism = Akkermansia muciniphila
SEQUENCE: 3
aacgaacgct ggcggcgtgg ataagacatg caagtcgaac gagagaattg ctagcttgct      60
aataattctc tagtggcgca cgggtgagta acacgtgagt aacctgcccc cgagagcgga     120
atagccctgg gaaactggga ttaataccgc atagtatcga aagattaaag cagcaatgcg     180
cttgggatg  ggctcgcggc ctattagtta gttggtgagg taacggctca ccaaggcgat     240
gacgggtagc cggtctgaga ggatgtccgg ccacactgga actgagacac ggtccagaca     300
cctacgggtg gcagcagtcg agaatcattc acaatgggg  aaaccctgat ggtgcgacgc     360
cgcgtgggg  aatgaaggtc ttcggattgt aaaccctgt  catgtgggag caaattaaaa     420
agatagtacc acaagaggaa gagacggcta actctgtgcc agcagccgcg gtaatacaga     480
ggtctcaagc gttgttcgga atcactgggc gtaaagcgtg cgtaggctgt ttcgtaagtc     540
gtgtgtgaaa ggcgcgggct caacccgcgg acggcacatg actagaagtaa                600
tggagggga  accggaattc tcggtgtagc agtgaaatgc gtagatatcg agaggaacac     660
tcgtggcgaa ggcgggttcc tggacattaa ctgacgctga ggcacgaagg ccaggggagc     720
gaaagggatt agataccct  gtagtcctgg cagtaaacgg tgcacgcttg gtgtgcgggg     780
aatcgacccc ctgcgtgccg gagtaacgcg ttaagcgtgc cgctggggga ctacggtcgc     840
aagattaaaa ctcaaagaaa ttgacgggga cccgcacaag cggtggagta tgtggcttaa     900
ttcgatgcaa cgcgaagaac cttacctggg cttgacatgt aatgaacaac atgtgaaagc     960
atgcgactct tcgaggcgt  tacacaggtg ctgcatggcc gtcgtcagct cgtgtcgtga    1020
gatgtttggt taagtccagc aacgagcgca accctgttg  ccagttacca gcacgtgaag    1080
gtggggactc tggcgagact gccagatca  actgggagga aggtggggac gacgtcaggt    1140
cagtatggcc cttatgccca gggctgcaca cgtactacaa tgcccagtac agaggggggcc   1200
gaagccgcga ggcggaggaa atcctaaaaa ctgggcccag ttcggactgt aggctgcaac    1260
ccgcctacac gaagccggaa tcgctagtaa tggcgcatca gctacggcgc cgtgaatacg    1320
ttcccgggtc ttgtacacac cgcccgtcac atcatggaag ctggtcgcac ccgaagtatc    1380
tgaagccaac cgcaaggagg cagggtccta aggtgagact ggtaactggg atg           1433

SEQ ID NO: 4             moltype = DNA   length = 1456
FEATURE                  Location/Qualifiers
source                   1..1456
                         mol_type = genomic DNA
                         organism = Anaerostipes caccae
SEQUENCE: 4
gcgcttaata catgtcaagt cgaacgaagc atttaggatt gaagttttcg gatggatttc      60
ctatatgact gagtggcgga cgggtgagta acgcgtgggg aacctgccct ataggggag     120
ataacagctg gaaacggctg ctaataccgc ataagcgcac agaatcgcat gattcagtgt     180
gaaaagccct ggcagtatag gatggtcccg cgtctgatta gctggttggt gaggtaacgg     240
ctcaccaagg cgacgatcag tagccggctt gagagagtga acggcacat  tgggactgag     300
acacggccca aactcctacg ggaggcagca gtggggaata ttgcacaatg ggggtaaacc     360
ctgatgcagc gacgccgcgt gagtgaagaa gtatttcggt atgtaaagct ctatcagcag     420
```

-continued

```
ggaagaaaac agacggtacc tgactaagaa gccccggcta actacgtgcc agcagccgcg    480
gtaatacgta gggggcaagc gttatccgga attactgggt gtaaagggtg cgtaggtggc    540
atggtaagtc agaagtgaaa gcccggggct taacccgggg actgcttttg aaactgtcat    600
gctggagtgc aggagaggta agcggaattc ctagtgtagc ggtgaaatgc gtagatatta    660
ggaggaacac cagtggcgaa ggcggcttac tggactgtca ctgacactga tgcacgaaag    720
cgtggggagc aaacaggatt agataccctg gtagtccacg ccgtaaacga tgaatactag    780
gtgtcggggc cgtagaggct tcggtgccgc agcaaacgca gtaagtattc cacctgggga    840
gtacgttcgc aagaatgaaa ctcaaaggaa ttgacgggga cccgcacaag cggtggagca    900
tgtggtttaa ttcgaagcaa cgcgaagaac cttacctggt cttgacatcc caatgaccga    960
accttaaccg gttttttctt tcgagacatt ggagacaggt ggtgcatggt tgtcgtcagc   1020
tcgtgtcgtg agatgttggg ttaagtcccg caacgagcgc aaccccctatc tttagtagcc   1080
agcatttaag gtgggcactc tagagagact gccaggggata acctggagga aggtggggac   1140
gacgtcaaat catcatgccc cttatggcca gggctacaca cgtgctacaa tggcgtaaac   1200
aaagggaagc gaagtcgtga ggcgaagcaa atcccaaaa taacgtctca gttcggattg   1260
tagtctgcaa ctcgactaca tgaagctgga atcgctagta atcgtgaatc agaatgtcac   1320
ggtgaatacg ttcccgggtc ttgtacacac cgcccgtcac accatgggag tcagtaacgc   1380
ccgaagtcag tgacccaacc gcaaggaggg agctgccgaa ggtgggaccg ataactgggg   1440
tgaagtcgta acaagg                                                   1456

SEQ ID NO: 5               moltype = DNA   length = 1466
FEATURE                    Location/Qualifiers
source                     1..1466
                           mol_type = genomic DNA
                           organism = Faecalibacterium prausnitzii
SEQUENCE: 5
gttgatcctg gctcaggacg aacgctggcg gcgcgcctaa cacatgcaag tcgaacgagc     60
gagagagagc ttgctttctc gagcgagtgg cgaacgggtg agtaacgcgt gaggaacctg    120
cctcaaagag ggggacaaca gttggaaacg actgctaata ccgcataagc ccacagctcg    180
gcatcgagca gagggaaaag gagcaatccg ctttgagatg gcctcgcgtc cgattagcta    240
gttggtggta taatgccca ccaaggcaac gatcggtagc cggactgaga ggttgaaacgg    300
ccacattggg actgagacac ggcccagact cctacgggag gcagcagtgg ggaatattgc    360
acaatggggg aaaccctgat gcagcgacgc cgcgtggagg aagaaggtct tcggattgta    420
aactcctgtt gttgaggaag ataatgacgg tactcaacaa ggaagtgacg ctaactacg    480
tgccagcagc cgcggtaaaa cgtaggtcac aagcgttgtc cggaattact gggtgtaaag    540
ggagcgcagg cgggaagaca agttggaagt gaaatctatg ggctcaaccc ataaactgct    600
ttcaaaactg ttttcttga gtagtgcaga ggtaggcgga attcccggtg tagcggtgga    660
atgcgtagat atcgggagga acaccagtgg cgaaggcggc ctactgggca ccaactgacg    720
ctgaggctcg aaagtgtggg tagcaaacag gattagatac cctggtagtc cacaccgtaa    780
acgatgatta ctaggtgttg gaggattgac cccttcagtg ccgcagttaa cacaataagt    840
aatccacctg gggagtacga ccgcaaggtt gaaactcaaa ggaattgacg ggggcccgca    900
caagcagtgg agtatgtggt ttaattcgac gcaacgcgaa gaaccttacc aagtcttgac    960
atcctgcgac gatgctggaa acagtatttt ccttcgggac gcagagacag gtggtgcatg   1020
gttgtcgtca gctcgtgtcg tgagatgttg gttaagtcc gcaacgagcg caaccctta   1080
ctgtcagtta ctacgcaaga ggactctggc aggactgccg ttgacaaaac ggaggaaggt   1140
ggggatgacg tcaaatcatc atgcccttta tgacttgggc tacacacgta ctaatggc   1200
gttaaacaaa gagaagcaag accgcgaggt ggagcaaaac tcagaaacaa cgtcccagtt   1260
cggactgcag gctgcaaatc gcctgcacga agtcggaatt gctagtaatc gtggatcagc   1320
atgccacggt gaatacgttc ccgggccttg tacacaccgc ccgtcacacc atgagagccg   1380
ggggacccg aagtcggtag tctaaccgca aggaggacgc cgccgaaggt aaaactggtg   1440
attggggtga agtcgtaaca aggtac                                        1466

SEQ ID NO: 6               moltype = DNA   length = 1586
FEATURE                    Location/Qualifiers
source                     1..1586
                           mol_type = genomic DNA
                           organism = Lactobacillus plantarum
SEQUENCE: 6
gggacatgct gcagtcgacg attagagttt gatcctggct caggacgaac gctggcggcg     60
tgcctaatac atgcaagtcg aacgaactct ggtattgatt ggtgcttgca tcatgattta    120
catttgagtg agtggcgaac tggtgagtaa cacgtggaa acctgcccag aagcggggga    180
taacacctgg aaacagatgc taataccgca taacaacttg gaccgcatgg tccgagtttg    240
aaagatggct tcggctatca cttttggatg gtcccgcggc gtattagcta gatggtgagg    300
taacggctta ccatggcaat gatacgtagc cgacctgaga gggtaatcgg ccacattggg    360
actgagacac ggcccaaact cctacgggag gcagcagtag gaatcttcc acaatggacg    420
aaagtctgat ggagcaacgc cgcgtgagtg aagaagggtt tcggctcgta aaactctgtt    480
gttaaagaag aacatatctg agagtaactg ttcaggtatt gacggtattt aaccagaaag    540
ccacggctaa ctacgtgcca gcagccgcgg taatacgtag gtggcaagcg ttgtccggat    600
ttattgggcg taaagcgagc gcaggcggtt ttttaagtct gatgtgaaag ccttcggctc    660
aaccgaagaa gtgcatcgga aactgggaaa cttgagtgca gaagaggaca gtggaactcc    720
atgtgtagcg gtgaaatgcg tagatatatg gaagaacacc agtggcgaag gcggctgtct    780
ggtctgtaac tgacgctgag gctcgaaagt atgggtagca acaggatta gatacctgg    840
tagtccatac cgtaaacgat gaatgctaag tgttggaggg tttccgccct tcagtgctgc    900
agctaacgca ttaagcattc cgcctgggga gtacggccgc aaggctgaaa ctcaaaggaa    960
ttgacggggg cccgcacaag cggtggagca tgtggtttaa ttcgaagcta cgcgaagaac   1020
cttaccaggt cttgacatac tatgcaaatc taagagatta cgttccct tcggggacat   1080
ggatacaggt ggtgcatggt tgtcgtcagc tcgtgtcgtg agatgttggg ttaagtcccg   1140
caacgagcgc aacccttatt atcagttgcc agcattaagt tgggcactct ggtgagactg   1200
ccggtgacaa accggaggaa ggtggggatg acgtcaaatc atcatgcccc ttatgacctg   1260
ggctacacac gtgctacaat ggatggtaca acgagttgcg aactcgcgag agtaagctaa   1320
```

```
tctcttaaag ccattctcag ttcggattgt aggctgcaac tcgcctacat gaagtcggaa    1380
tcgctagtaa tcgcggatca gcatgccgcg gtgaatacgt tcccgggcct tgtacacacc    1440
gcccgtcaca ccatgagagt ttgtaacacc caaagtcggt ggggtaacct tttaggaacc    1500
agccgcctaa ggtgggacag atgattaggg tgaagtcgta acaaggtaac caatctctag    1560
aggtccccgg gaccgagctg acgcaa                                         1586

SEQ ID NO: 7            moltype = DNA  length = 1482
FEATURE                 Location/Qualifiers
source                  1..1482
                        mol_type = genomic DNA
                        organism = Butyricicoccus pullicaecorum
SEQUENCE: 7
tagtttgatc ctggctcagg atgaacgctg gcggcgtgcc taacacatgc aagtcgaacg     60
gagttgtttg aggaaatcct tcgggatgga atcttccaac ttagtggcgg acgggtgagt    120
aacgcgtgag caatctgcct ttcagagggg gataacagcc ggaaacggct gctaataccg    180
cataatgcat tgaattcgca tgttttgat gccaaagatt ttatcgctga aagatgagct     240
cgcgtctgat tagctagttg gcggggtaac ggcccaccaa ggcgacgatc agtagccgga    300
ctgagaggtt gaacggccac attgggactg aggacacggc ccagactcct accgggaggc    360
agcagtgggg aatattgcgc aatgggggca accctgacgc agcaacgccg cgtgattgat    420
gaaggtcttc ggattgtaaa aatctttaat cagggacgaa acaaatgacg gtacctgaag    480
aataagctcc ggctaactac gtgccagcag ccgcggtaat acgtagggag caagcgttat    540
ccggatttac tgggtgtaaa gggcgtgtag gcgggcttgt aagttggaag tgaaatctcg    600
gggcttaacc ccgaaactgc tttcaaaact gcgagtcttg agtgatggag aggcaggcgg    660
aattcccagt gtagcggtga aatgcgtaga tattgggagg aacaccagtg gcgaaggcgg    720
cctgctggac attaactgac gctgaggcgc gaaagcgtgg ggagcaaaca ggattagata    780
ccctggtagt ccacgccgta aacgatggat actaggtgtg aagtgtattg accccttccg    840
tgccggagtt aacacaataa gtatcccacc tggggagtac ggccgcaagg ttgaaactca    900
aaggaattga cgggggcccg cacaagcagt ggagtatgtg gtttaattcg aagcaacgcg    960
caagaaccttt accaagtctt gacatcccga tgaccgctcy agagatagg cttttcttcg   1020
gaacatcggt gacaggtggt gcatggttgt cgtcagctcg tgtcgtgaga tgttgggtta   1080
agtcccgcaa cgagcgcaac ccttacgggt tagttgctac gcaagagcac tctagccgga   1140
ctgccgttga caaacggag gaaggtgggg acgacgtcaa atcatcatgc ccttatgac    1200
ttgggctaca cacgtactac aatggcagtc atacagaggg aagcaaaacc gcgaggtgga   1260
gcaaatccct aaaagctgtc ccagttcaga ttgcaggctg caactcgcct gcatgaagtc   1320
ggaattgcta gtaatcgcgg atcagcatgc cgcggtgaat acgttcccgg gccttgtaca   1380
caccgcccgt cacaccatga gagccggtaa tacccgaagt ccgtagtcta accgcaagga   1440
ggacgcggcc gaaggtagga ctggtaattg ggacgaagtc gt                      1482

SEQ ID NO: 8            moltype = DNA  length = 23
FEATURE                 Location/Qualifiers
misc_feature            1..23
                        note = DNA primer
source                  1..23
                        mol_type = other DNA
                        organism = synthetic construct
SEQUENCE: 8
tatggactat gttgtaatag gac                                             23

SEQ ID NO: 9            moltype = DNA  length = 23
FEATURE                 Location/Qualifiers
misc_feature            1..23
                        note = DNA primer
source                  1..23
                        mol_type = other DNA
                        organism = synthetic construct
SEQUENCE: 9
cataatattg ggtctattcc tac                                             23
```

USE OF MICROBIAL COMMUNITIES FOR HUMAN AND ANIMAL HEALTH

CROSS-REFERENCE TO RELATED APPLICATIONS

This application is a continuation U.S. application Ser. No. 17/502,445, filed Oct. 15, 2021, which is a continuation of U.S. patent application Ser. No. 17/386,266, filed Jul. 27, 2021, which is a continuation of U.S. patent application Ser. No. 16/068,470, filed Jul. 6, 2018, now U.S. Pat. No. 11,096,971, issued Aug. 24, 2021, which is a national phase entry under 35 U.S.C. § 371 of International Patent Application PCT/EP2017/052422, filed Feb. 3, 2017, designating the United States of America and published as International Patent Publication WO 2017/134240 A1 on Aug. 10, 2017, which claims the benefit under Article 8 of the Patent Cooperation Treaty to European Patent Application Serial No. EP16154288.1, filed Feb. 4, 2016, the contents of the entirety of each of which are incorporated herein by this reference.

TECHNICAL FIELD

This application relates to a mixture of bacteria belonging to at least six or seven different and specific bacterial species, preferably for use to prevent or treat gastro-intestinal disorders. More preferably, the mixture of bacteria is grown together in a fermenter prior to administering the mixture to a subject in order to prevent or treat the disorder.

STATEMENT ACCORDING TO 37 C.F.R. § 1.821(c) or (e)-SEQUENCE LISTING SUBMITTED AS XML FILE

Pursuant to 37 C.F.R. § 1.821(c) or (e), a file containing an XML version of the Sequence Listing has been submitted concomitant with this application, the contents of which are hereby incorporated by reference. Said copy, created on Oct. 3, 2022, is named 202046-701306_SL.xml and is 20,480 bytes in size.

BACKGROUND

The human and animal gut ecosystem consists of a variety of different habitats and metabolic niches that are colonized by the so-called microbiota that contain more than $10^{11}$ micro-organisms per gram wet weight of contents, predominantly anaerobes (Macfarlane & Macfarlane, 1997). It is nowadays well-recognized that the human or animal gut microbiome plays a crucial role in human health and well-being by contributing to energy harvest, modulating the immune system and establishing colonization resistance against opportunistic pathogens (Fuller & Gibson, 1997; Cummings & Macfarlane, 1997). Evidence exists that the interaction of bacteria and their metabolites with the mucus layer and/or with the intestinal gut wall is important (Barnett et al. 2012). Although the gut microbiome is generally stable over time, its composition is altered by external perturbations, such as dietary changes, antibiotic use, increasing hygienization and stress. This leads to an unbalanced condition in the gastrointestinal tract, called dysbiosis (Clemente et al. 2012). Dysbiosis is characterized by moderate or severe disruptions in the normal gut microbiome composition, thereby causing the lack of key microbial species, gaps in specific microbial functions and, as a consequence, an impaired modulation of the gut wall activity. This may lead to the colonization of pathogenic microorganisms—causing diarrhea or necrotizing enteritis (Sekirov et al. 2008). One of the extreme forms of such pathogenesis is CDAD (Clostridium difficile associated diarrhea) for which classic antibiotic therapy is more and more falling short of curing the patient. Other consequences of microbial dysbiosis may be a compromised immune response, resulting in chronic inflammation (Willing et al. 2009) or food allergies, or an increased gut permeability, nutrient malabsorption or even bacteremia. The adverse effects of dysbiosis toward microbial functionality and gut wall physiology may thus undermine human health. In fact, constipation, IBS, IBD, pouchitis, metabolic syndrome, obesity, diabetes, cardiovascular diseases, mental conditions, impaired cognitive function, a neurodegenerative disease, different types of cancers (e.g., colon cancer), inflammation of the female reproductive apparatus, CDAD, rheumatism or rheumatoid arthritis are all associated with changes in the activity/composition of the gut microbiota. It is, therefore, clear that dysbiosis should be avoided or remedied upon occurrence.

When dysbiosis is associated with the presence of pathogens, an obvious strategy to get rid of health-detrimental microorganisms is the application of antibiotic agents. However, widespread and improper use of broad-spectrum antibiotics over the last decades has dramatically increased antibiotic resistance (Brandi et al. 2008). Moreover, antibiotics also tackle the indigenous gut microorganisms, many of which fulfill crucial functions and deliver health benefits, therefore worsening the condition of dysbiosis. As a result, the last two decades have seen a tremendous increase in functional food research, particularly the development of prebiotic and probiotic products. Although the prebiotic concept is attractive as it concerns the dietary modulation of indigenous gut microorganisms that are already adapted to the host (Van Loo et al. 1999), it is primarily used in a preventive manner. For a therapeutic application, a severely disrupted gut microbiome would benefit more from the introduction of key microbial species, rather than the provision of substrates that benefit health-promoting species that are less abundant or even absent in a diseased individual. A possible solution is the introduction of viable, health-promoting microorganisms, termed probiotics (Iannitti and Palmieri, 2010). Probiotic products are mostly comprised of one to a couple of not interconnected microbial strains (mostly lactic acid-producing bacteria) with a specific functionality. However, survival of probiotic strains during the harsh conditions of the upper digestive tract is challenging and competition with the vast indigenous microbiome is often negligible. Yet, the concept of introducing new species in a compromised gut ecosystem has gained momentum in recent years through the application of fecal microbial transplants (FMT) (Khoruts et al. 2010). This entails the transfer of a fecal microbial slurry from a healthy donor to a diseased recipient. This form of bacteriotherapy is mostly applied to treat antibiotic-resistant infections and has cure rates of 90% and higher. FMT is currently being considered for treating many other pathologies that have their origin in gastrointestinal dysbiosis (Crohn's disease, obesity, irritable bowel syndrome, etc.). FMT seems to efficiently work where single probiotic strains frequently fail. Yet, the badly characterized nature of fecal transplants comes with transmission risks of infectious diseases and currently raises questions over its widespread applicability in less acute and life-threatening pathologies (De Vrieze 2013).

Early 2013, an alternative for fecal microbial transplants entered the field with the publication of a scientific paper (Petrof et al. 2013) and patent application (WO 2013/037068—Method for treatment of disorders of the gastro-intestinal system) on the use of a synthetic mixture of microbes that were isolated from an individual based on their culturability as therapeutic agent to cure CDAD. Such product is also composed of a known set of microorganisms, which would take away the concerns of disease transmission from fecal transplants, when QPS criteria are respected. However, mixing together microorganisms does not guarantee them to interact with one another and to occupy functional niches that require microbial networking. Product stability, standardization and performance of important functions can, therefore, not be guaranteed.

In the patent application WO 2014/145958A2 (Network-based microbial compositions and methods), it is proposed to administer to a mammalian subject, in need of an effective amount of a therapeutic bacterial composition, a plurality of isolated bacteria or a purified bacterial preparation. The plurality of isolated bacteria or the purified bacterial preparation is able to form a so-called network ecology. The bacteria belonging to this preparation are selected based on genomic information and are provided to the mammalian subject as a loosely assembled set of strains.

In a publication of Becker et al. (2011), a community is described consisting of eight different strains: *Anaerostipes caccae*, *Bacteroides thetaiotaomicron*, *Bifidobacterium longum*, *Blautia producta*, *Clostridium butyricum*, *Clostridium ramosum*, *Escherichia coli*, and *Lactobacillus plantarum*. The community is referred to as SIHUMIx (Simplified Human Microbiota extended). This artificial microbial community was tested in rat studies, comparing SIHUMIx-inoculated rats with conventional human-associated and germ-free rats. The authors claim the community is representative for the human colon-associated microbiota in terms of composition and functionality. The microbial community evolved depending on the age of the rats, but reached a stable composition over time.

Van den Abbeele et al. (2013) suggested the possibility of creating a glycan-degrading community by using conventional in vitro fermenters that can be inoculated with relevant keystone species and a mixture of cross-feeding microbes. After inoculation and stabilization, such a microbial network unit for specific functions can be attained and produced at a large scale.

Finally, Newton et al. (1998) made use of anaerobic chemostats to create reproducible defined bacterial communities comprising fourteen different saccharolytic and amino acid-fermenting species (i.e., *Bifidobacterium longum*, *Bif. adolescentis*, *Bif. pseudolongum*, *Bif. infantis*, *Bacteroides thetaiotaomicron*, *Bact. vulgatus*, *Lactobacillus acidophilus*, *Enterococcus faecalis*, *Ent. faecium*, *Escherichia coli*, *Clostridium perfringens*, *Cl. butyricum*, *Cl. innocuum* , *Cl. Bifermentans*) to study the effect of the sulphate-reducing bacterium (SRB) *Desulfovibrio desulfuricans* on other intestinal organisms.

However, there is still a need to design alternative and specific mixtures of bacterial species that can be effectively used to prevent or treat gastro-intestinal disorders. Moreover, it is completely unknown whether pre-adapted mixtures perform therapeutically as well, worse or better when compared to administering the loosely assembled and non-pre-adapted mixtures of the same bacterial species.

BRIEF SUMMARY

This disclosure relates in the first instance to a composition consisting essentially of bacteria belonging to the species *Faecalibacterium prausnitzii*, *Butyricicoccus pullicaecorum*, *Roseburia inulinivorans*, *Roseburia hominis*, *Akkermansia muciniphila*, *Lactobacillus plantarum* and *Anaerostipes caccae* preferably for use to prevent or treat symptoms associated with a gastro-intestinal disorder.

In other words, the disclosure relates to a method of preventing or treating symptoms associated with a gastro-intestinal disorder in a subject in need thereof, the method comprising administering to the subject a therapeutically effective amount of a composition consisting essentially of bacteria belonging to the species *Faecalibacterium prausnitzii*, *Butyricicoccus pullicaecorum*, *Roseburia inuliniv- orans*, *Roseburia hominis*, *Akkermansia muciniphila*, *Lactobacillus plantarum* and *Anaerostipes caccae*.

This disclosure further relates to a composition as described wherein the gastro-intestinal disorder is a disruption of the barrier function of the gut, diarrhea, constipation, irritable bowel syndrome, inflammatory bowel disease, Crohn's disease, ulcerative colitis, coeliac disease, pouchitis, mucositis, an infection of the gut, gut microbiota dysbiosis, or any combination thereof.

Also disclosed is a composition as described herein, wherein the gastro-intestinal disorder is prevented or treated via: a) stimulating growth and/or activity of one or a limited number of beneficial bacteria in the intestinal tract, b) inhibiting growth and/or activity of one or a limited number of pathogenic bacteria in the intestinal tract, c) relatively increasing the attachment of non-pathogenic bacteria to the mucosa of the gastrointestinal surface, d) reducing uncontrolled uptake of antigens, pro-inflammatory, bacteria or bacterial products by the gut, e) providing anti-inflammatory activity at the intestinal surface, f) increasing gut barrier functioning, g) producing bacterial metabolites or h) any combination of a) to g).

The disclosure also relates to a composition as described herein wherein bacteria belonging to the species *Roseburia hominis* are eliminated from the composition.

The disclosure further relates to a composition as described herein wherein bacteria belonging to the species *Escherichia coli*, *Enterococcus faecium*, *Lactobacillus mucosae*, *Bifidobacterium adolescentis*, *Bifidobacterium longum*, *Bacteroides thetaiotaomicron* and *Bacteroides vulgatus* are further added to the composition.

The disclosure further relates to a composition as described herein further comprising one or more prebiotics.

In a preferred embodiment, this disclosure relates to a composition as described herein wherein the bacteria are preadapted by growing them together in a fermenter prior to administering the composition to the subject to prevent or treat the gastro-intestinal disorders.

In this regard, the disclosure further relates to a composition as described herein wherein the fermenter is a dynamic simulator of the gastro-intestinal tract.

More specifically, this disclosure relates to a composition as described herein wherein the bacteria are chosen from the list of the following strains: *Faecalibacterium prausnitzii* LMG P-29362, *Faecalibacterium prausnitzii* DSMZ 17677, *Butyricicoccus pullicaecorum* LMG P-29360, *Butyricicoccus pullicaecorum* LMG 24109, *Roseburia inulinivorans* LMG P-29365, *Roseburia inulinivorans* DSMZ 16841, *Roseburia hominis* LMG P-29364, *Roseburia hominis* DSMZ 16839, *Akkermansia mucimphila* LMG P-29361, *Akkermansia mucimphila* DSMZ 22959, *Lactobacillus plantarum* LMG P-29366, *Lactobacillus plantarum* ZJ316, *Anaerostipes caccae* LMG P-29359, *Anaerostipes caccae* DSMZ 14662 and/or strains showing at least 97% sequence identity to the 16SrRNA sequences of at least one of the strains.

The disclosure further relates to a composition as described herein wherein the composition is a pharmaceutical composition formulated either as a rectally administrated form or an orally ingestible form.

In this regard, the disclosure further relates to a composition as described herein wherein the orally ingestible form is a capsule, microcapsule, tablet, granule, powder, troche, pill, suspension or syrup.

The disclosure further relates to a composition as described herein that is incorporated in a food, drink, food supplement or nutraceutical.

This disclosure more specifically relates to a composition as described herein wherein the composition comprises between $10^5$ and $10^{11}$ colony-forming units of bacteria.

The gut microbiome comprises hundreds of microbial species that co-exist within different subjects and that interact with each other and the host. Nowadays, it is generally believed that the gut microbiota play a key role in human health and disease by regulating metabolic functions and immune homeostasis (Cent et al. 2014). Several studies have investigated these complex gut microbial communities in an attempt to define a "core microbiome," implying that all human individuals share a key number of essential species or strains that define the functional capabilities of a healthy gut microbiome (Kinross et al., 2011). Based on this concept (i.e., that all humans are populated by a core microbiome), the extensive literature that is available on the composition and function of the gut microbiota (e.g., keystone species, mucosal versus luminal microbiota, proximal versus distal colon bacteria, etc.) and functional genome analysis, a list of microbial candidates could be identified that covers the main functionalities of the complex human gut microbiome.

The disclosure relates in the first instance to a specific selection of a subgroup of bacterial species of the human gut microbiome that have a particular and surprising effect. More specifically, the disclosure relates to a composition consisting essentially of bacteria belonging to the species *Faecalibacterium prausnitzii, Butyricicoccus pullicaecorum, Roseburia inulinivorans, Roseburia hominis, Akkermansia muciniphila, Lactobacillus plantarum* and *Anaerostipes caccae* preferably for use to prevent or treat symptoms associated with a gastro-intestinal disorder. The term "consisting essentially of" indicates that the composition may include other bacterial species and/or other components provided they do not negatively affect the effect (i.e., preventing or treating symptoms associated with a gastro-intestinal disorder) of the composition. In an embodiment, a composition of the disclosure comprises bacteria belonging to the species *Faecalibacterium prausnitzii, Butyricicoccus pullicaecorum, Roseburia inulinivorans, Roseburia hominis, Akkermansia muciniphila, Lactobacillus plantarum* and *Anaerostipes caccae*.

In another embodiment, a composition of the disclosure consists of bacteria belonging to the species *Faecalibacterium prausnitzii, Butyricicoccus pullicaecorum, Roseburia inulinivorans, Roseburia hominis, Akkermansia muciniphila, Lactobacillus plantarum* and *Anaerostipes caccae*.

The bacterial species *Faecalibacterium prausnitzii* (Duncan et al. 2002), *Butyricicoccus pullicaecorum* (Eeckhaut et al. 2008), *Roseburia inulinivorans* (Duncan et al. 2006), *Roseburia hominis* (Duncan et al. 2006), *Akkermansia muciniphila* (Derrien et al. 2004), *Lactobacillus plantarum* (Walter 2008) and *Anaerostipes caccae* (Schwiertz et al. 2002) are well-known bacterial species to a skilled person. The terms "symptoms associated with a gastro-intestinal disorder" refer to health problems in humans and animals. The use of a composition of the disclosure leads more specifically to prevention/recovery from dysbiosis resulting in a positive modulation of the interaction between bacteria and intestinal surface. As a result, an improved functioning of the intestinal surface is obtained: e.g., barrier, hormonal, immune functioning. The onset of the effect on the intestinal surface is quicker when a "pre-adapted composition" is dosed as compared to a "loosely assembled set of the same strains" (see further). As used herein, modulating or improving the barrier, hormonal or immune function of the intestinal surface is meant to include altering any parameter that affects the normal homeostasis of the intestinal surface and, in particular, its role in the first line of defense against the invasion by pathogens, antigens or other harmful substances and its role to produce substances (e.g., immune molecules, hormones) that have systemic influences on the host. The parameters include, but are not limited to:

a stimulation of the growth and/or activity of one or a limited number of beneficial bacteria in the intestinal tract (e.g., lactobacilli, bifidobacteria, butyrate- or propionate-producing bacteria, others);

an inhibition of the growth and/or activity of one or a number of pathogenic bacteria in the intestinal tract;

a relative increase in the attachment of non-pathogenic bacteria to the mucosa of the intestinal surface;

a reduction in the uncontrolled uptake from the gut of antigens, pro-inflammatory molecules, bacteria or bacterial products;

modulation of the gut-associated lymphoid tissue (GALT) and the host systemic immune system;

production of specific bacterial metabolites (e.g., propionate, butyrate); and modulation of the production of certain intestinal signaling molecules that directly or indirectly modulate metabolic homeostasis (e.g., pro-glucagon, GLP-1, GLP-2, FIAF).

This disclosure thus relates to a composition as described herein wherein the gastro-intestinal disorder is prevented or treated via: a) stimulating growth and/or activity of one or a limited number of beneficial bacteria in the intestinal tract, b) inhibiting growth and/or activity of one or a limited number of pathogenic bacteria in the intestinal tract, c) relatively increasing the attachment of non-pathogenic bacteria to the mucosa of the gastrointestinal surface, d) reducing uncontrolled uptake of antigens, pro-inflammatory, bacteria or bacterial products by the gut, e) providing anti-inflammatory activity at the intestinal surface, f) increasing gut barrier functioning, g) producing bacterial metabolites or h) any combination of a) to g).

Health conditions that may be associated with general gastro-intestinal disorders include, but are not limited to, constipation, Irritable Bowel Syndrome (IBS), Inflammatory Bowel Diseases (IBD), gut microbiota dysbiosis, mucositis, metabolic syndrome, obesity, diabetes, a cardiovascular disease, chronic fatigue syndrome, a mental condition, impaired cognitive function, a neurodegenerative disease, a form of cancer, an autoimmune condition, impaired immune functioning, rheumatism, rheumatoid arthritis, inflammation of the female reproductive apparatus, and infection of pathogens (bacteria, viruses and fungi). Examples of neurodegenerative diseases include, but are not limited to, ALS, dementia, Alzheimer's, Parkinson's and Huntington's disease. Examples of types of cancers include, but are not limited to, lung cancer, breast cancer, prostate cancer, pancreatic cancer and particularly colorectal cancer. Examples of autoimmune diseases include, but are not limited to, multiple sclerosis, atopic dermatitis, celiac disease, psoriasis and lupus.

Based on the observation that the compositions of the disclosure enhance the interaction and/or activity of non-pathogenic bacteria to the mucosal layer of the gastrointestinal epithelium, it is envisaged that the preparations are particularly useful to improve the barrier function of the intestinal surface, such as, for example, to prevent or reduce the uncontrolled uptake from the gut of antigens, pro-inflammatory molecules, pathogenic bacteria or bacterial products. One such indication with an impaired mucosal barrier is Inflammatory Bowel Disease. As it is generally accepted that in Inflammatory Bowel Diseases, mucosal injury with an impaired resolution of the lesions is one of the key elements that lead to these chronic indications, the compositions of the disclosure have a beneficial effect in that indication. Provided is the use of the compositions of the disclosure in the prevention and treatment of conditions associated with an impaired barrier function and characterized by the uncontrolled uptake from the gut of antigens, pro-inflammatory molecules, pathogenic bacteria or bacterial products.

"Inflammatory bowel diseases," also referred to as "chronic colonic diseases," as used herein include any condition characterized by persistent mucosal inflammation at different levels of the gastrointestinal tract, such as, for example, inflammatory bowel syndrome, mucositis, gastric ulcers, Crohn's disease, ulcerative colitis, colorectal cancer and pouchitis.

As mucositis is generally recognized as being essentially characterized by inflammation of the mucosal surface lining the mouth and gastrointestinal tract, typically as adverse event of chemotherapy and radiotherapy or stem cell transplantation, it is also to be envisaged that the application of the compositions of the disclosure have a beneficial effect in that indication. Thus, also provided herein is the use of the compositions of the disclosure in the prevention and treatment of conditions associated with mucositis. Mucositis can occur anywhere along the gastrointestinal tract. In the case of occurring in the oral cavity, it is typically referred to as oral mucositis.

It is also to be envisaged that the application of the compositions of the disclosure provide protection against introduction of antigens that cause allergic reactions, whereby such allergens may comprise certain food substances, chemicals and other molecules. Thus, in a further embodiment, provided is the use of compositions in the prevention and treatment of conditions associated with the introduction of antigens leading to allergic reactions (e.g., food allergies, asthma, and eczema).

It is furthermore also envisaged that the application of the compositions to influence both the gut-associated lymphoid tissue (GALT) as well as the systemic immune system. Among other effects, this may result in decreased expression of pro-inflammatory cytokines and increased production of immunoregulatory factors and improved activity of lymphocytes. It is, therefore, envisaged that the compositions be particularly useful in improving the development and functioning of the host immune system.

In another aspect of the disclosure, based on the observation that the compositions of the disclosure modulate the epithelial barrier and subsequently decrease chronic inflammation, it is envisaged that the compositions be particularly useful in controlling and improving metabolic homeostasis. Non-limiting effects of the preparations on metabolic homeostasis include control of food intake and fat and glucose metabolism, improvement of insulin secretion and sensitivity and control of cholesterol synthesis and metabolism. Thus, also provided herein is the use of the compositions of the disclosure in the management of food uptake, induction of satiety, weight management, and the prevention and treatment of conditions associated with an impaired metabolic homeostasis, such as obesity and type 2 diabetes.

Based on the observation that a composition of the disclosure decreases several established causal risk factors of cardiovascular diseases (CVD), it is to be envisaged in another aspect of the disclosure that the compositions be particularly useful for the prevention of CVD. CVD technically refers to any disease that affects the cardiovascular system, yet is usually used to refer to those related to atherosclerosis. The latter is a syndrome affecting arterial blood vessels, a chronic inflammatory response in the walls of arteries, in large part due to the accumulation of macrophage white blood cells and promoted by low density lipoproteins. CVD development depends on multiple mechanisms and a number of clear causal risk factors have been identified. These factors include, yet are not limited to, elevated LDL cholesterol, plasma triglycerides, metabolic diseases (obesity, diabetes, etc.), chronic inflammation and oxidative stress. The latter two factors are especially of utmost importance. Atherosclerosis develops from LDL becoming oxidized (LDL-ox) by free radicals, particularly oxygen free radicals, in situations of oxidative stress. Excessive response of the immune system, in case of chronic inflammation, to damage caused by LDL-ox further promotes the expansion of the disease. Thus, also provided herein is the use of the compositions of the disclosure in the prevention or treatment of CVD.

In a further aspect, given the beneficial effect of the compositions of the disclosure on the adherence of the normal microbiota to the mucosal layer, it is envisaged that the application of the compositions provides protection against mucosal attachment and invasion by pathogens. Examples of pathogens include, but are not limited to, *Bacillus anthracis, Bacillus cereus, Bordetella pertussis, Borrelia burgdorferi, Brucella abortus, Brucella canis, Brucella melitensis, Brucella suis, Campylobacter jejuni, Chlamydia pneumonia, Chlamydia trachomatis, Chlamydophila psittaci, Clostridium botulinum, Clostridium difficile, Clostridium perfringens, Clostridium tetani, Corynebacterium diphtheria, Enterotoxigenic Escherichia coli* (ETEC), *Enteropathogenic E. coli, E. coli* O157:H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumonia, Streptococcus pyogenes, Treponema pallidum, Vibrio cholera, Yersinia pestis, Candida* spp., *Norovirus* (Norwalk Virus), and *Hepatitis A*, and viruses inducing smallpox, influenza, mumps, measles, chickenpox, ebola, and rubella. Thus, in a further embodiment, the disclosure provides the use of the compositions of the disclosure in the prevention and treatment of conditions associated with the mucosal attachment and invasion by pathogens, in particular, in the treatment and prevention of acquired diarrhea and traveler's diarrhea.

The disclosure thus relates to a method to prevent or treat symptoms associated with a gastro-intestinal disorder in a subject in need thereof comprising administering a therapeutically effective amount of a composition consisting essentially of bacteria belonging to the species *Faecalibacterium prausnitzii, Butyricicoccus pullicaecorum, Roseburia inulinivorans, Roseburia hominis, Akkermansia muciniphila, Lactobacillus plantarum* and *Anaerostipes caccae*.

The term "subject in need" refers to a human or a non-human animal having a gastro-intestinal disorder as described herein.

The terms "a therapeutically effective amount" refers to a minimum of the combined total amount of the seven bacterial species that is capable of exerting its prophylactic or therapeutic effect. The seven bacteria species are *Faecalibacterium prausnitzii, Butyricicoccus pullicaecorum, Roseburia inulinivorans, Roseburia hominis, Akkermansia muciniphila, Lactobacillus plantarum* and *Anaerostipes caccae*.

However, "a therapeutically effective amount" may also refer to a minimum of a combined total amount of six bacteria species: *Faecalibacterium prausnitzii, Butyricicoccus pullicaecorum, Roseburia inulinivorans, Akkermansia muciniphila, Lactobacillus plantarum* and *Anaerostipes caccae*.

Depending on the final application, the combined total amount can be the result of equal amounts of each of the seven bacterial species or unequal amounts of the seven bacterial species, in which each single species of the seven bacterial species has a minimum abundance of 0.0001% of the combined total amount, more preferably a minimum abundance of 0.001% of the combined total amount and most preferably a minimum abundance of 0.01% of the combined total amount. If thus, for example, six species have an abundance of 10.00% of the combined total amount, then the seventh species has an abundance of 40.00% of the combined total amount. Depending on the final application, the combined total amount ranges between a daily dose of $10^2$ and $10^{14}$ bacterial cells, preferably ranging between a daily dose of $10^3$ and $10^{13}$ bacterial cells, more preferably ranging between a daily dose of $10^4$ and $10^{12}$ bacterial cells and most preferably ranging between a daily dose of $10^5$ and $10^{11}$ bacterial cells.

The disclosure further relates to a composition as described herein wherein bacteria belonging to the species Roseburia hominis are eliminated from the composition. The term "eliminated" refers, in particular, to making a composition of six bacterial species as is indicated further in the Examples section without adding or removing the species *Roseburia hominis* as a seventh species.

The disclosure further relates to a composition as described herein wherein bacteria belonging to the species *Escherichia coli, Enterococcus faecium, Lactobacillus mucosae, Bifidobacterium adolescentis, Bifidobacterium longum, Bacteroides thetaiotaomicron* and *Bacteroides vulgatus* are further added to the composition.

The bacterial species *Escherichia coli* (Rath et al. 1999), *Enterococcus faecium* (Schleifer et al. 1984), *Lactobacillus mucosae* (Roos et al. 2000), *Bifidobacterium adolescentis* (Scharek et al. 2000), *Bifidobacterium longum* (Bahaka et al. 1993), *Bacteroides thetaiotaomicron* (Scharek et al. 2000) and *Bacteroides vulgatus* (Rath et al. 1999) are well known bacterial species to a skilled person. The disclosure further relates to a composition as described herein further comprising one or more prebiotics.

The term "prebiotic" refers to any chemical that induces the growth or activity of microorganisms (e.g., bacteria) that contribute to the well-being of their host. Hence, prebiotics can influence or alter the composition of organisms in the gut microbiome. However, in principle, it is a more general term that can refer to other areas of the body as well. Typical, but non-limiting, prebiotics are non-digestible fiber compounds that at least partially pass undigested through the upper part of the gastrointestinal tract and stimulate the growth or activity of advantageous bacteria that colonize the large bowel by acting as substrate for them.

In a preferred embodiment, the disclosure relates to a composition as described herein wherein the bacteria are grown together in a fermenter prior to administering the composition to prevent or treat the gastro-intestinal disorders. The latter compositions are also referred to (see further) as the "Collaborome strategy" or as the "Alternative collaborome strategy." In contrast, compositions wherein the bacteria are not grown together in a fermenter prior to administration are referred to (see further) as the "Assembly strategy."

In this regard, this disclosure further relates to a composition as described herein wherein the fermenter is a dynamic simulator of the gastro-intestinal tract. In this specific case, the latter compositions are also referred to (see further) as the "Collaborome strategy."

The SHIME® (Simulator of the Human Microbial Ecosystem) is a dynamic in vitro model of the human gastrointestinal tract that is composed of five double-jacketed vessels, simulating the stomach, small intestine, and the three colon regions (ascending, transverse, and descending colon), with a total retention time of 72 hours (FIG. 1). Three times per day, 140 ml SHIME® feed and 60 ml pancreatic juice were added to the stomach and small intestine compartments, respectively (Van den Abbeele et al., 2010). After an initial two-week stabilization period, which allows the microbiota to adapt to the imposed in vitro conditions, the isolation procedure was started. The selected microbial strains of the disclosure can thus be inoculated in single-stage (alternative collaborome strategy) or multi-stage reactors or dynamic simulators of the gastrointestinal tract (e.g., SHIME® or M-SHIME®, collaborome strategy) under standardized conditions representative for the GI tract. Accordingly, the disclosure relates to a reactor comprising a composition comprising, consisting of or consisting essentially of bacteria belonging to six or seven or up to fourteen species as defined herein and further listed below:

comprising a composition comprising, consisting of or consisting essentially of bacteria belonging to the species *Faecalibacterium prausnitzii, Butyricicoccus pullicaecorum, Roseburia inulinivorans, Roseburia hominis, Akkermansia muciniphila, Lactobacillus plantarum*, and *Anaerostipes caccae*, or comprising a composition comprising, consisting of or consisting essentially of bacteria belonging to the species *Faecalibacterium prausnitzii, Butyricicoccus pullicaecorum, Roseburia inulinivorans, Akkermansia muciniphila, Lactobacillus plantarum*, and *Anaerostipes caccae* or, comprising a composition comprising, consisting of or consisting essentially of bacteria belonging to the species *Faecalibacterium prausnitzii, Butyricicoccus pullicaecorum, Roseburia inulinivorans, Roseburia hominis, Akkermansia muciniphila, Lactobacillus plantarum, Anaerostipes caccae, Escherichia coli, Enterococcus faecium, Lactobacillus mucosae, Bifidobacterium adolescentis, Bifidobacterium longum, Bacteroides thetaiotaomicron*, and *Bacteroides vulgatus*.

In a preferred embodiment, this reactor comprising the composition is under standardized conditions representative for the GI tract as defined below.

The parameters characterizing the standardized conditions include, but are not limited to, pH (ranging between 1.5 and 8); availability of carbon sources (either carbohydrate or proteins or a combination thereof); retention time in a specific reactor (ranging between 10 minutes and 200 hours); oxygen availability (ranging between 0 and 8 g/L);

availability of micronutrients; presence/absence of antibiotics; concentration of bile salts (ranging between 0 and 20 mM); presence of heavy metals; and presence of host factors as immune molecules. In a preferred embodiment, the parameters characterizing the standardized conditions comprise pH, retention time in a specific reactor and concentration of bile salts, all as earlier defined herein. Depending on the complexity of the collaborome, a period of 1 to 15 days is needed to obtain a functionally stable collaborome. On average, in order to develop a collaborome composed of 7 to 14 members, a time between 3 and 10 days is sufficient to obtain a functionally stable collaborome (depending on the environmental conditions). A composition as defined herein is, therefore, obtainable after having been trained or cultured during a time between 3 and 10 days under conditions wherein pH, retention time in a specific reactor, and concentration of bile salts have been set as defined herein. Such a process allows the production of a composition or collaborome that is functionally stable.

Within the context of the disclosure, "a functionally stable collaborome" is a composition as defined herein still comprising the initial different number of species of bacteria after at least 3 or 5 or 10 days of culture.

In a further aspect, there is provided a reactor operating under standardized conditions representative for the GI tract, comprising: pH ranging between 1.5 and 8; availability of carbon sources; retention time between 10 minutes and 200 hours; oxygen availability between 0 and 8 g/L; availability of micronutrients; presence/absence of antibiotics; concentration of bile salts between 0 and 20 mM; presence of heavy metals; and presence of host factors as immune molecules. In an embodiment, the reactor is such that the parameters characterizing the standardized conditions comprise pH, retention time in a specific reactor and concentration of bile salts as defined in the previous paragraph. In an embodiment, such reactor comprises a composition of 5 and 20 distinct bacteria members, or 6 to 14 distinct bacteria members or 5 to 15 distinct bacteria members. In a preferred embodiment, such composition resides for a time between 3 and 14 days or 3 and 10 days in such a reactor to obtain a functionally stable collaborome.

The disclosure more specifically relates to the composition and use of a set of microbial strains having specific functional characteristics and pre-adapted to function together in order to prevent or treat health problems in humans and animals and obtaining a faster biotherapeutic onset and higher efficiency as compared to a loosely assembled set of the same strains (="assembly strategy"). Such a set of microorganisms pre-adapted to function together takes the name of the "collaborome strategy" or "alternative collaborome strategy."

In other words, the disclosure relates to pre-adapted compositions of sets of microbial strains preferably for use to significantly decrease the time of biotherapeutic onset and/or to significantly increase the effect of treatment of dysbiosis as compared to a loosely assembled set of the same microbial strains.

The terms "significantly decrease the time of biotherapeutic onset" mean that, by being pre-adapted, the set of microorganisms can exert their functionality at least 5% quicker (on a temporal scale), preferably at least 10% quicker, more preferably at least 20% quicker and most preferably at least 30% quicker as compared to a loosely assembled set of the same strains. Any value below 5% is considered physiologically not relevant.

The terms "significantly increase the effect of treatment" mean that, by being pre-adapted, the set of microorganisms can exert their functionality with at least a 5% higher efficacy, preferably at least 10% more efficient, more preferably at least 20% and most preferably at least 30% more efficient. The efficacy depends on the endpoint for which the set of microorganisms has been designed. Possible functionalities include, but are not limited to, Short Chain Fatty Acid (SCFA) production, improvement in gut barrier permeability, decrease/increase in pro-inflammatory cytokines, increase in anti-inflammatory cytokines, decrease in pathogen concentration (at least 0.5 log), decrease in gas production, and stimulation of specific gut-wall receptors, etc. Any value below 5% is considered physiologically not relevant.

Hence, the disclosure more specifically relates to a method to prevent or treat dysbiosis of humans and animals in need thereof comprising administering a therapeutic amount of a pre-adapted composition of a set of microbial strains to the humans or animals wherein the treatment results in a faster biotherapeutic onset and/or increased efficiency as compared to the administration of a loosely assembled set of the same microbial strains.

More specifically, the disclosure relates to a composition as described herein wherein the bacteria are chosen from the list of the following strains: *Faecalibacterium prausnitzii* LMG P-29362, *Faecalibacterium prausnitzii* DSMZ 17677, *Butyricicoccus pullicaecorum* LMG P-29360, *Butyricicoccus pullicaecorum* LMG 24109, *Roseburia inulinivorans* LMG P-29365, *Roseburia inulinivorans* DSMZ 16841, *Roseburia hominis* LMG P-29364, *Roseburia hominis* DSMZ 16839, *Akkermansia muchyphila* LMG P-29361, *Akkermansia muchyphila* DSMZ 22959, *Lactobacillus plantarum* LMG P-29366, *Lactobacillus plantarum* ZJ316, *Anaerostipes caccae* LMG P-29359, *Anaerostipes caccae* DSMZ 14662 and/or strains showing at least 97% sequence identity to the 16SrRNA sequences of at least one of the strains.

The above-indicated strains having accession numbers LMG P-29362 (date of deposit: Jan. 18, 2016), LMG P-29360 (date of deposit: Jan. 18, 2016), LMG P-29365 (date of deposit: Jan. 18, 2016), LMG P-29364 (date of deposit: Jan. 18, 2016), LMG P-29361 (date of deposit: Jan. 18, 2016), LMG P-29366 (date of deposit: Jan. 18, 2016) and LMG P-29359 (date of deposit: Jan. 18, 2016) have been deposited with BCCM/LMG Laboratorium voor Microbiologie, Universiteit Gent (UGent), having an address of K. L. Ledeganckstraat 35, B-9000 Gent, Belgium.

The above-indicated strains having accession numbers DSMZ 17677, LMG24109, DSMZ 16841, DSMZ 16839, DSMZ 22959, ZJ316 and DSMZ 14662 have been deposited in public collections, have been described intensively and are accessible to skilled persons worldwide.

It should be further clear that variants of each of the strains showing at least 97% (i.e., 97, 98, 99%) sequence homology to the 16S rRNA sequence of each of the corresponding strains are also part of this disclosure. An example to determine such sequence "homology" is, for instance, described by Eeckhaut et al. (2008). As used herein, the term "16S rRNA" refers to a nucleic acid sequence of about 1542 nucleotides, which is a component of the small prokaryotic ribosomal subunit (30S). The 16S rRNA is known to act as a scaffold defining the positions of the ribosomal proteins. The 16S rRNA sequence is commonly used for phylogenetic studies, as it is known to be a highly conserved sequence. Comparative analysis of 16S rRNA sequences from thousands of organisms has demonstrated the presence of oligonucleotide signature sequences. As used herein, the term "homology" refers to the sequence similarity of the nucleic acids. For example, in general, if two nucleic acids have identical sequences they show 100% homology. A change in the nucleotide sequence of one of the nucleic acids reduces the percentage of homology. In general, the percentage homology quantifies the degree of identity between two nucleic acid sentences.

Sequence identity or sequence homology is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by various methods, known to those skilled in the art. In a preferred embodiment, sequence identity is determined by comparing the whole length of the sequences as identified herein.

Preferred methods to determine identity are designed to give the largest match between the sequences tested. Methods to determine identity and similarity are codified in publicly available computer programs. Preferred computer program methods to determine identity and similarity between two sequences include, e.g., the BestFit, BLASTP, BLASTN, and FASTA (S. F. Altschul et al., *J. Mol. Biol.* 215:403-410 (1990), publicly available from NCBI and other sources (BLAST Manual, S. Altschul et al., *NCBI NLM NIH* Bethesda, Md. 20894). A most preferred algorithm used is EMBOSS (on the World Wide Web at ebi-.ac.uk/emboss/align). Preferred parameters for amino acid sequences comparison using EMBOSS are gap open 10.0, gap extend 0.5, Blosum 62 matrix. Preferred parameters for nucleic acid sequences comparison using EMBOSS are gap open 10.0, gap extend 0.5, DNA full matrix (DNA identity matrix).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and Val to ile or leu.

It is well known to a person skilled in the art that 16s rRNA sequences can be deposited online, for example, at GenBank (on the World Wide Web at ncbi.nlm.nih.gov/genbank/) and that they can be retrieved based on their unique accession number for use as reference 16S rRNA sequence in evaluation of sequence homology, such as, for example, described by Eeckhaut et al. (2008). The GenBank accession numbers for the 16S rRNA sequences of seven bacterial species of the composition are listed below. These accession numbers can be used to retrieve the respective 16S rRNA sequences from the World Wide Web at ncbi.nlm.nih-.gov/genbank/ for assessment of sequence homology.

| Species | Strain | GenBank accession number (ncbi.nlm.nih.gov/genbank/) |
| --- | --- | --- |
| *Roseburia hominis* | DSMZ 16839 | AJ270482.2 (SEQ ID NO: 1) |
| *Roseburia inulinivorans* | DSMZ 16841 | AJ270473.3 (SEQ ID NO: 2) |
| *Akkermansia muciniphila* | DSMZ 22959 | AY271254.1 (SEQ ID NO: 3) |
| *Anaerostipes caccae* | DSMZ 14662 | AJ270487.2 (SEQ ID NO: 4) |
| *Faecalibacterium prausnitzii* | DSMZ 17677 | AJ270469.2 (SEQ ID NO: 5) |
| *Lactobacillus plantarum* | ZJ316 | JN126052.1 (SEQ ID NO: 6) |
| *Butyricicoccus pullicaecorum* | LMG 24109 | HH793440.1 (SEQ ID NO: 7) |

The disclosure further relates to a composition as described herein wherein the composition is a pharmaceutical composition formulated either as a rectally administrated form or an orally ingestible form.

In this regard, the disclosure further relates to a composition as described herein wherein the orally ingestible form is a capsule, microcapsule, tablet, granule, powder, troche, pill, suspension or syrup.

This disclosure further relates to a composition as described herein that is incorporated in a food, drink, food supplement or nutraceutical.

The disclosure thus relates to a composition as described herein that is used as food, food supplement or medicine for a human, a non-human domestic or farmed land animal or an aquatic animal. The composition can thus be introduced in food, functional foods, food supplements, cosmetics, nutraceutical formulations, probiotic composition or pharmaceutical. A food is typically an edible material composed primarily of one or more of the macronutrients protein, carbohydrate and fat. A food may also contain one or more micronutrients such as vitamins or minerals. The term food as used herein also covers a beverage. Examples of foods in which the composition may be incorporated include snack bars, cereals, buns, muffins, biscuits, cakes, pastries, processed vegetables, sweets, probiotic formulations including yogurts, beverages, plant oil-based liquids, animal fat-based liquids, frozen confections and cheeses. Preferred foods include yogurts, cheeses and other dairy products. Examples of beverages include soft beverages, syrups, squashes, dry drink mixes and nutritional beverages. A nutraceutical is a food ingredient, food supplement or food product that is considered to provide a medical or health benefit, including the prevention and treatment of disease. A functional food is a food that is typically marketed as providing a health benefit beyond that of supplying pure nutrition to the consumer.

Also provided is a probiotic comprising a composition as discussed herein. A probiotic is typically a live supplement that can enhance the intestinal microbiota. Such probiotics may be given in particular to humans but also to farm and domestic animals and to aquatic organisms. The probiotic may additionally comprise one or more acceptable excipients or flavorings, which are suitable for ingestion by a human or animal.

A composition of the disclosure may be used in the production of pharmaceutical compositions. Thus, further provided is a pharmaceutical composition comprising a composition of the disclosure and a pharmaceutically acceptable excipient or carrier.

Compositions comprising compounds of the disclosure may be in diverse forms, for example, in the form of a tablet, capsule, or powder. Examples of excipients that may be present in such compositions include diluents (e.g., starch, cellulose derivatives or sugar derivatives), a stabilizer (e.g., hygroscopic excipients such as silica or maltodextrin), a lubricant (e.g., magnesium stearate), a buffer (e.g., phosphate buffer), a binder, coating, preservative or suspension agent. Suitable excipients are well known to those skilled in the art.

This disclosure more specifically relates to a composition as described herein wherein the composition comprises a total between $10^5$ and $10^{11}$ colony-forming units of bacteria of the disclosure.

In this document and in its claims, the verb "to comprise" and its conjugations is used in its non-limiting sense to mean that items following the word are included, but items not specifically mentioned are not excluded. In addition, the verb "to consist" may be replaced by "to consist essentially of" meaning that a composition as defined herein may comprise additional component(s) than the ones specifically identified, the additional component(s) not altering the unique characteristic of the disclosure. In addition, reference to an element by the indefinite article "a" or "an" does not exclude the possibility that more than one of the elements are present, unless the context clearly requires that there be one and only one of the elements. The indefinite article "a" or "an" thus usually means "at least one."

All patent and literature references cited in the present specification are hereby incorporated by reference in their entirety. The included examples are offered for illustrative purposes only, and are not intended to limit the scope of the disclosure in any way.

DETAILED DESCRIPTION

EXAMPLES

Figure 1:
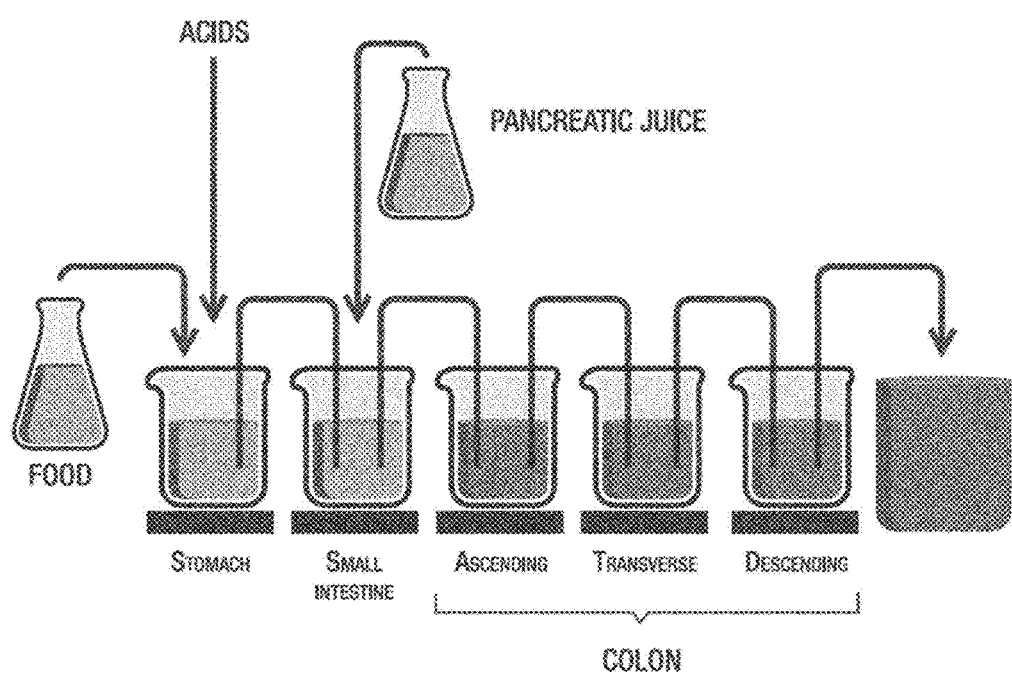
FIG. 1: Schematic representation of a SHIME® unit that consists of stomach, small intestine, and the three different colon regions. Liquid SHIME® nutritional medium and pancreatic juice enter the compartments, which simulate the stomach and small intestine, respectively. After a defined residence time in these sterile compartments, the suspension goes to three consecutive colon compartments, the ascending, transverse, and descending colon compartments, each characterized by distinct pHs and residence times. These compartments are inoculated with human fecal microbiota. All vessels are kept anaerobic by flushing the headspace with N2, continuously stirred, and kept at 37° C.

Example 1: Establishment of a Composition 1.1 Isolation of Bacteria for the Composition A young, healthy donor with no prior exposure to antibiotic therapy was selected to inoculate the SHIME® model. By controlling several operational parameters of the SHIME® model (FIG. 1, Van den Abbeele et al., 2010), one can enrich and select for networks of gut microbiota that have a beneficial impact on human health such as microbiota involved in dietary fiber fermentation, bile acids metabolism, lactose degradation, etc. The SHIME® setup was used for isolation of bacterial strains with different functional properties, such as fiber degraders (e.g., *Bifidobacteria, Bacteroides*), fermentative (e.g., *Escherichia coli*) or lactate producers (e.g., Lactobacilli, Pediococci and Enterococci), butyrate producers (e.g., *Anaerostipes caccae, Butyricicoccus pullicaecorum, Faecalibacterium prausnitzii , Roseburia hominis, Roseburia inulinivorans, Clostridium butyricum*) and propionate producers (e.g., *Bacteroides thetaiotaomicron, Bacteroides vulgatus, Roseburia inulinivorans, Akkermansia muciniphila*). For this purpose, certain media were selected such as LAMVAB (lactobacilli; Hartemink et al. 1997), RB (bifidobacteria; Hartemink et al. 1996), Enterococcus medium (Enterococci; Possemiers et al. 2004), TBX (*Escherichia coil*; Le Bon et al. 2010), BBE (*Bacteroides fragilis* group; Livingston et al. 1978), Mucin minimal medium (Akkermansia; Derrien et al. 2004), M2GSC (butyrate producers; Barcenilla et al. 2000) or lactate-containing minimal SHIMS® medium (butyrate producers), succinate- and fucose-containing minimal SHIMS® media (propionate producers), sulphate-enriched minimal media (sulphate reducers), arabinoxylan-containing minimal SHIME® medium and Blood agar plates (Prevotella). In addition to the SHIME®, bacteria were also isolated directly from a fresh fecal sample from a healthy donor, using the same strategy.

In practice, ten-fold dilutions of samples collected from the colonic compartments of the SHIME® or homogenized fecal samples were made and spread on agar plates with the specific medium composition as described herein. Plates were incubated at 37° C., taking into account the respective growth conditions of the different bacterial groups. Upon incubation, approximately 30 colonies were picked up per bacterial group and incubated in the respective liquid growth media under appropriate conditions. The short-chain fatty acid concentrations in the overnight cultures were analyzed using gas chromatography as described in Possemiers et al. (2004). Furthermore, a sample of the liquid cultures was used for phylogenetic analysis. DNA was extracted as described in Possemiers et al. 2004 and the near-entire 16S rRNA sequences were amplified for each isolate using the universal eubacterial primers fD1 and rD1 (Weisburg et al. 1991). Upon purification, the DNA samples were sent out for sequencing. The obtained sequences were aligned with existing sequences for identification of each isolate using the BLAST toolbox (on the World Wide Web at blast.ncbi.nlm.nih.gov/Blast.cgi).

1.2 Design of the Composition

To combine different bacterial strains into actual functional microbial networks, the pure cultures isolated from the SHIME® reactor and fecal were used (as described in Example 1.1). Additionally, pure cultures were sourced from culture collections such as BCCM/LMG (World Wide Web at bccm.belspo.be) and DSMZ (World Wide Web at dsmz.de).

Short-chain fatty acids (SCFA) are the end products of dietary fibers fermentation by the intestinal microbiota and are known to exert several beneficial effects on host health. The main SCFA produced are acetate, butyrate and propionate in an approximate 60:20:20 molar ratio. Whereas acetate can be absorbed from the gut and used as energy substrate by the host, butyrate acts as the main energy source for the gut epithelium and has proven protective effects against inflammation and colon cancer. Propionate has similar local activity in the gut as compared to butyrate, yet it is also transported to the liver where it was shown to have positive cholesterol-lowering effects and effects on glycemic control.

Considering the important and diverse physiological roles of SCFA, disruption of this gut microbial function (e.g., in gastrointestinal disorders) can have a significant impact on host health. Consequently, in this example, a screening was performed to design a composition that can induce the highest total SCFA production and most interesting relative SCFA production ratios. For the latter, butyrate was considered the most interesting among the different SCFA produced. Furthermore, the effect of the different compositions on gut barrier integrity was assessed by means of a co-culture of epithelial and immune cells.

In practice, a total 20 isolates with the most interesting fermentation profiles, obtained from the isolation and selection round as described in 1.1 (referred to as "Isolate-X") or ordered from culture collections, were retrieved from their glycerol stocks and grown under their respective optimal growth conditions to obtain homogeneous suspensions of the bacterial strains.

| Ref. | Species | Strain |
| --- | --- | --- |
| 1 | Lactobacillus plantarum | Isolate-1 |
| 2 | Clostridium bolteae | Isolate-2 |
| 3 | Desulfovibrio desulfuricans | Isolate-3 |
| 4 | Akkermansia muciniphila | Isolate-4 |
| 5 | Coprococcus spp. | Isolate-5 |
| 6 | Roseburia hominis | Isolate-6 |
| 7 | Bacteroides thetaiotaomicron | Isolate-7 |
| 8 | Clostridium butyricum | Isolate-8 |
| 9 | Anaerostipes caccae | Isolate-9 |
| 10 | Bifidobacterium adolescentis | Isolate-10 |
| 11 | Faecalibacterium prausnitzii | Isolate-11 |
| 12 | Roseburia inulinivorans | Isolate-12 |
| 13 | Ruminococcus spp. | Isolate-13 |
| 14 | Lactobacillus acidophilus | Isolate-14 |
| 15 | Enterococcus faecium | Isolate-15 |
| 16 | Butyrivibrio fibrisolvens | Isolate-16 |
| 17 | Eubacterium limosum | DSM20543 |
| 18 | Escherichia coli | Nissle 1917 |
| 19 | Eubacterium rectale | DSM17629 |
| 20 | Butyricicoccus pullicaecorum | Isolate-17 |

Isolates were combined in numbers ranging from 2 to 10 in a set of 98 individual initial screening experiments. For each experiment, fermentation was started in sterile incubation bottles containing sterilized SHIME® nutritional medium adjusted to pH 6.8 with $KH_2PO_4/K_2HPO_4$ and flushed with nitrogen. Then, the sterilized medium was inoculated with 10% (v/v) of mixed inoculum consisting of equal volumes of the selected species. Incubation bottles were flushed with nitrogen to ensure anaerobic conditions and were incubated at 37° C. (90 rpm). Samples were analyzed after 24 hours for SCFA production. Compositions with the highest butyrate production were then selected and further used in the final experiment with 23 different sets of bacteria (referred to as MX-Y, in which X=number of isolates present in the composition and Y=unique composition A, B, C, etc. with X isolates).

| Identification number | Composition |
| --- | --- |
| M2-A | 10, 12 |
| M3-A | 1, 9, 11 |
| M4-A | 1, 5, 10, 11 |
| M4-B | 8, 10, 11, 17 |
| M4-C | 9, 10, 11, 13 |
| M5-A | 5, 8, 10, 13, 18 |
| M5-B | 6, 9, 10, 11, 18 |
| M6-A | 5, 6, 9, 10, 12, 14 |
| M6-B | 2, 4, 8, 11, 13, 19 |
| M6-C | 1, 4, 9, 11, 12, 17 |
| M6-D | 1, 6, 11, 13, 16, 20 |
| M7-A | 1, 3, 6, 9, 12, 16, 20 |
| M7-B | 1, 4, 6, 9, 11, 12, 20 |
| M7-C | 6, 7, 13, 14, 16, 17, 20 |
| M8-A | 4, 5, 6, 9, 10, 11, 13, 17 |
| M8-B | 4, 6, 7, 8, 11, 14, 16, 18 |
| M8-C | 1, 4, 8, 11, 12, 15, 17, 20 |
| M9-A | 3, 6, 7, 11, 13, 14, 15, 17, 20 |
| M9-B | 3, 4, 6, 7, 14, 15, 16, 18, 20 |
| M9-C | 2, 3, 5, 6, 7, 8, 12, 14, 20 |
| M10-A | 1, 3, 4, 7, 8, 9, 10, 12, 14, 15 |
| M10-B | 3, 4, 5, 7, 8, 9, 12, 14, 15, 16, 19 |
| M10-C | 2, 4, 6, 8, 10, 11, 12, 13, 16, 18 |

These 23 combinations were again incubated as described before. After 24 hours, samples were collected for SCFA analysis and for combination with the co-culture model of Caco-2 and THP1 cells, as described in Possemiers et al. (2013). Endpoint of the latter experiment was Trans-Epithelial Electrical Resistance (TEER) as measured for protective effects toward gut barrier function.

Figure 2:
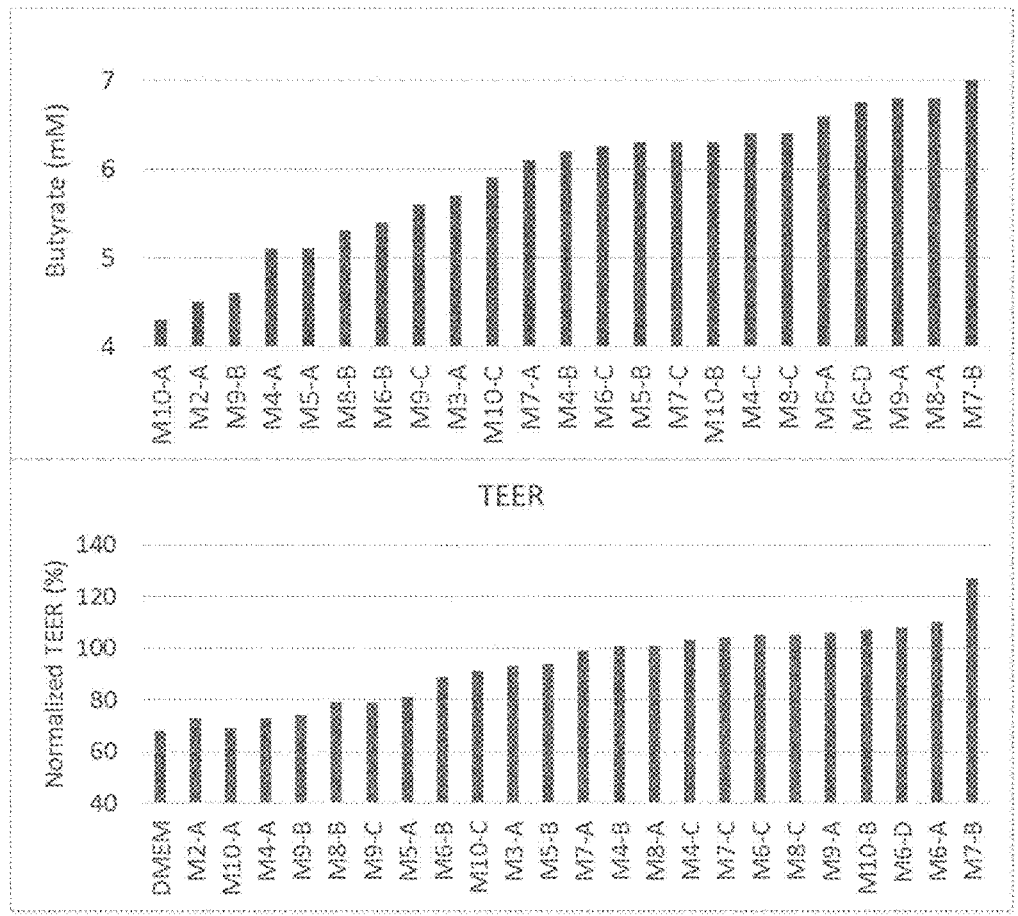
FIG. 2: Butyrate production by 23 different compositions upon 24-hour incubation (top panel) and effect on the transepithelial electrical resistance (TEER) of Caco-2 cells cultured in the presence of THP1 cells (bottom panel). For the latter, samples collected from the 23 incubations after 24 were sterile-filtered and added (1:5 v/v) for 24 hours to the apical compartment of Caco-2 cells grown for fourteen days on semipermeable inserts and placed on top of PMA-stimulated THP1-derived macrophages (co-cultures). Growth medium alone (DMEM) was used as control. THP1 cells cultured in the presence of PMA for 48 hours induce damage on the Caco-2 cells as measured by a decrease in TEER in the DMEM control. TEER values have been normalized to the values measured before co-culture (0 hour) and are expressed as percentage from the initial value. The coding of the different compositions was as follows: MX-Y, in which X=number of isolates present in the composition and Y=unique composition A, B, C, etc., with X isolates.

FIG. 2 describes butyrate levels obtained upon 24-hour incubation of the 23 different compositions as well as their effect on the TEER values. Strong variation was observed in both butyrate levels and effects on gut barrier functioning and combinations with highest butyrate levels did not necessarily induce highest protective effects on TEER levels, as shown by different ranking. Surprisingly, one composition of seven different isolates (referred to as M7-B in FIG. 2) was ranked first on both butyrate levels after 24 hours and especially on protective effects toward gut barrier function. This composition contained six isolates from the SHIME® and one culture obtained from a human fecal sample. 16S rRNA gene sequencing and comparison of the sequence with the NCBI BLAST database revealed that M7-B was composed of novel SHIME® isolates of *Lactobacillus plantarum, Faecalibacterium prausnitzii, Roseburia inulinivorans, Roseburia hominis, Akkermansia muciniphila* and *Anaerostipes caccae* and of a novel fecal isolate of *Butyricicoccus pullicaecorum*. Interestingly, the novel isolates were all present in at least one of the other compositions shown in FIG. 2, yet none of the other compositions reached the same effectivity with respect to butyrate production and protection of TEER values. This shows that the observed effect is not related to one of the specific species present in the composition, but that only the specific combination of these seven bacteria leads to the surprising positive results.

The seven novel isolates were deposited at the BCCM/LMG Bacteria collection (Ghent Belgium), with accession numbers: *Faecalibacterium prausnitzii* LMG P-29362, *Butyricicoccus pullicaecorum* LMG P-29360, *Roseburia inulinivorans* LMG P-29365, *Roseburia hominis* LMG P-29364, *Akkermansia mucimphila* LMG P-29361, *Lactobacillus plantarum* LMG P-29366 and *Anaerostipes caccae* LMG P-29359.

Figure 3:
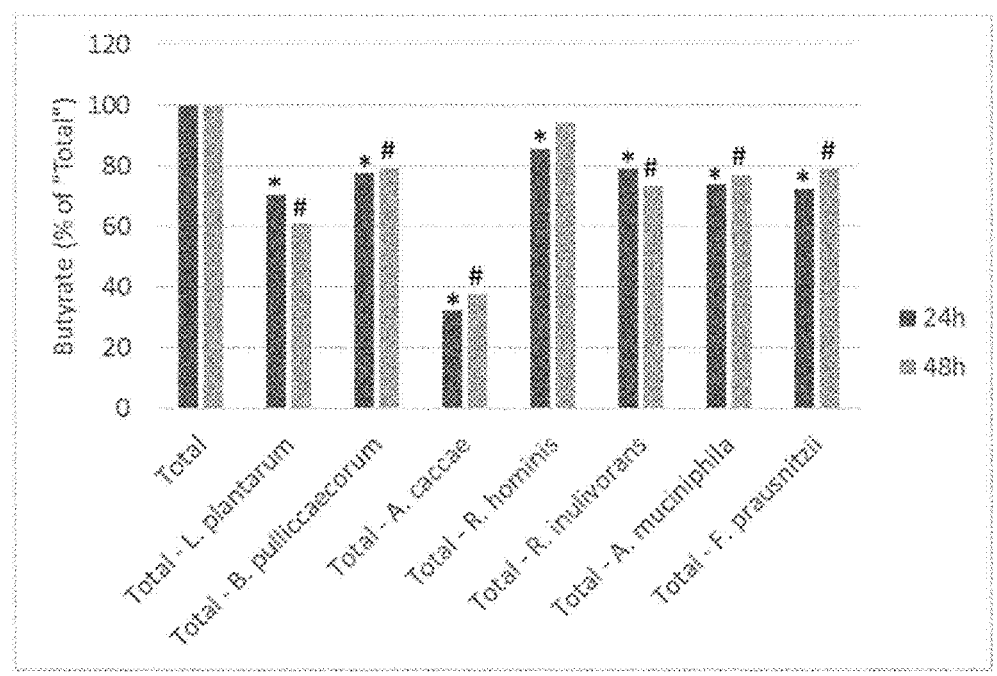
FIG. 3: Butyrate production upon 24-hour and 48-hour incubation in conditioned SHIME® nutritional medium by either the complete composition of seven species or compositions of six species, in which each time one of the seven original species was omitted. Results are presented as the percentage of butyrate production detected in each incubation with a composition of six species, as opposed to the composition consisting of all seven species. Compositions are referred to as "Total" (all seven species) or "Total—X," with X being the species omitted from the total composition. *: $p<0.05$ as compared to "Total" at 24 hours; #: $p<0.05$ as compared to "Total" at 48 hours.

As additional experimental evidence of the surprising synergy between the seven isolates and the need for presence of each of the species, an experiment was set up in which each time one of the isolates was removed (i.e., eliminated) from the original composition of seven isolates. In practice, fermentation was started again in sterile incubation bottles containing sterilized SHIME® nutritional medium adjusted to pH 6.8 with $KH_2PO_4/K_2HPO_4$ and flushed with nitrogen. Then, the sterilized medium was inoculated with 10% (v/v) of mixed inoculum consisting of equal volumes of six of the seven isolates. The complete composition of seven isolates acted as control, resulting in a total of eight parallel incubations. Incubation bottles were flushed with nitrogen to ensure anaerobic conditions and were incubated at 37° C. (90 rpm). Samples were analyzed after 24 hours and 48 hours for butyrate production. As shown in FIG. 3, removal of only one species out of the original composition significantly decreased butyrate production levels after 24 hours for all compositions of six species to below 80% of the butyrate production of the original composition. Also, after 48 hours of incubation, butyrate levels were significantly lower for all compositions of six species, with the exception of the composition excluding *Roseburia hominis*. This confirms that all isolates of the composition are essential to reach the full potential of the composition. As only the composition excluding *Roseburia hominis* still resulted in a similar functionality of the complete composition after 48 hours of incubation, one can also envisage, as second best, the use of the composition of six species, consisting essentially of *Faecalibacterium prausnitzii, Butyricicoccus pullicaecorum, Roseburia inulinivorans, Akkermansia mucimphila, Lactobacillus plantarum* and *Anaerostipes caccae*.

1.3 Production of the Composition

A composition consisting of the species *Lactobacillus plantarum, Faecalibacterium prausnitzii, Butyricicoccus pullicaecorum, Roseburia inulinivorans, Roseburia hominis, Akkermansia mucimphila* and *Anaerostipes caccae* is produced using three different strategies. These strategies include either 1) growing the species of the composition separately, followed by mixing them together, 2) growing the species of the composition together in a multi-stage fermenter (i.e., the in vitro SHIME® model as described herein) and 3) growing the species of the composition together in a single-stage fermenter.

Figure 4:
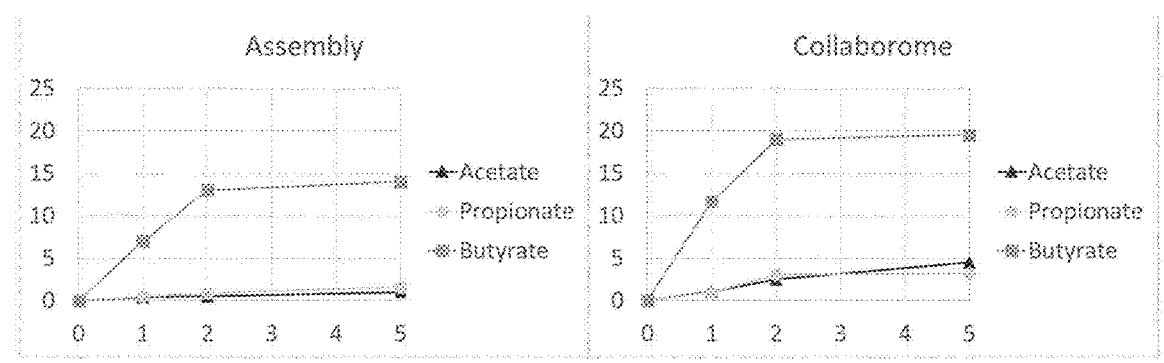
FIG. 4: Levels (mM) of butyrate, propionate and acetate produced by the composition throughout a five-day anaerobic incubation in conditioned SHIME® nutritional medium. The composition was either produced through the "Assembly" strategy (left panel) or the "Collaborome" strategy (right panel).

In the first strategy (the "assembly" strategy), the selected species were retrieved from their glycerol stocks and grown under their respective optimal growth conditions to obtain homogeneous suspensions of the bacterial strains. To evaluate their functional activity, a mixed inoculum was created consisting of equal volumes of the selected species. This inoculum was added at 10% (v/v) to sterile incubation bottles containing sterilized SHIME® nutritional medium adjusted to pH 6.8 with $KH_2PO_4/K_2HPO_4$. Incubation bottles were flushed with nitrogen to ensure anaerobic conditions and were incubated at 37° C. (90 rpm). At specific intervals of 16 hours, 40% (v:v) of the growth medium was replaced with conditioned SHIME® nutritional medium. Conditioned SHIME® nutritional medium was prepared by incubating 700 mL of normal SHIME® feed (pH 2) for one hour at 37° C., after which 300 mL of pancreatic juice (pH 6.8)—supplemented with 25 g/L NaHCO3, 23.6 g/L $KH_2PO_4$ and 4.7 g/L $K_2HPO_4$—was added. Samples were analyzed over a period of five days for SCFA production (FIG. 4). Butyrate levels reached 7 mM upon 24 hours incubation of the assembly and a maximum of 14 mM after five days.

Figure 5:
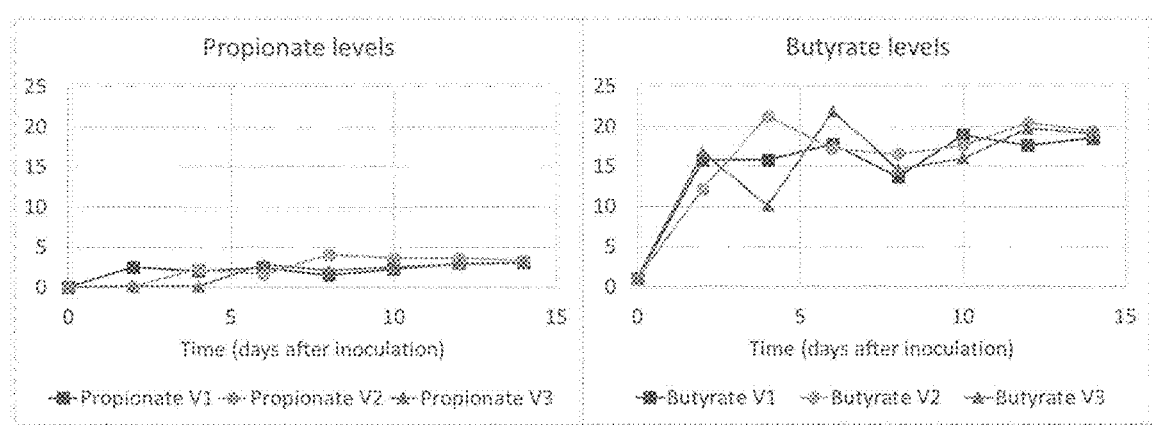
FIG. 5: Evolution of the levels (mM) of propionate (left panel) and butyrate (right panel) over a fourteen-day time period in three independent production cycles of the composition through the "Collaborome" strategy. Upon initial growth in appropriate culture medium, the strains of the composition were mixed, inoculated and cultured for fourteen days in triplicate in a SHIME® setup, consisting of a single colon region at a pH of 6.15-6.4.

In the second strategy (i.e., the "Collaborome" strategy or the strategy "wherein the bacteria are grown together in a dynamic simulator of the gastro-intestinal tract prior to administration"), the selected species were retrieved from their glycerol stocks and grown under their respective optimal growth conditions to obtain homogeneous suspensions of the bacterial strains. Then, the strains were mixed and inoculated in triplicate in a SHIME® setup (Van den Abeele et al., 2010) consisting of a single colon region at a pH of 6.15-6.4. A two-week adaptation period was implemented to create a functional collaborome composition. The need and relevance of such an adaptation period is clearly demonstrated by the evolution of SCFA profiles during the cultivation of the composition of selected species (FIG. 5). Initially, the composition requires time to adapt to one another and to become active in converting the supplied substrates to SCFA. However, four to six days after inoculation, the production of SCFA by the composition started to stabilize and high levels of butyrate were measured. On the final day of incubation (day 14), each of the triplicate incubations resulted in a highly similar, stable and strongly active functional composition with butyrate levels reaching 19 mM.

When the stabilized Collaborome was frozen at −80° C. as glycerol stock and subsequently thawed for use as inoculum in the same way as for the assembly strategy, butyrate levels surprisingly increased faster and reached 25% higher levels under the same incubation conditions as for the assembly of individual species (FIG. 4). Butyrate levels already reached 12 mM upon 24-hour incubation of the assembly and a maximum of 19 mM was already reached after two days.

In the third strategy, the production of the composition was undertaken using an optimized single-stage fermenter approach, operated in fed-batch mode (i.e., the alternative "Collaborome" strategy or the strategy "wherein the bacteria are grown together in "a fermenter prior to administration"). The selected species were retrieved from their glycerol stocks and grown under their respective optimal growth conditions to obtain homogeneous suspensions of the bacterial strains. Fermentation was started in sterile incubation bottles containing sterilized SHIME® feed adjusted to pH 6.8 with $KH_2PO_4/K_2HPO_4$ and flushed with nitrogen. Then, the sterilized medium was inoculated with 10% (v/v) of mixed inoculum consisting of equal volumes of the selected species. Incubation bottles were flushed with nitrogen to ensure anaerobic conditions and were incubated at 37° C. (90 rpm). At specific intervals of 16 hours, 40% (v:v) of the growth medium was replaced with conditioned SHIME® nutritional medium. Conditioned SHIME® nutritional medium was prepared by incubating 700 mL of normal SHIME® feed (pH 2) for one hour at 37° C., after which 300 mL of pancreatic juice (pH 6.8)—supplemented with 25 g/L NaHCO3, 23.6 g/L $KH_2PO_4$ and 4.7 g/L $K_2HPO_4$—was added.

Figure 6:
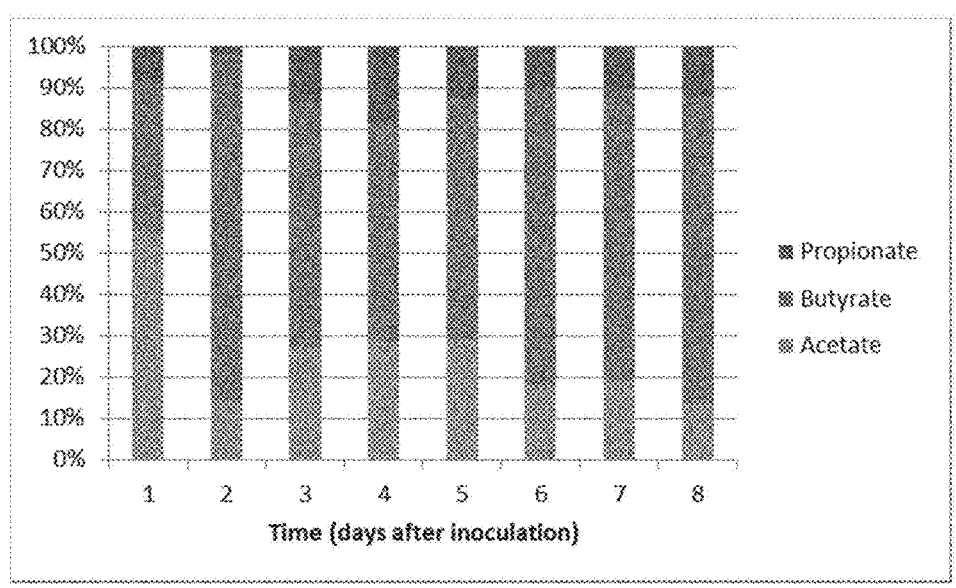
FIG. 6: Evolution of SCFA levels expressed as mol % of acetate, propionate and butyrate over time, upon production of the composition through the alternative "Collaborome" strategy. Upon initial growth in appropriate culture medium, the strains of the composition were mixed, inoculated and cultured for eight days in triplicate in single fermenters operated in a fed-batch mode. At specific intervals of 16 hours, 40% (v:v) of the growth medium was replaced with conditioned SHIME® nutritional medium.

As shown in FIG. 6, the total SCFA production and the ratio of SCFA produced by the composition was stable after six replacement cycles. When re-inoculated in the same strategy as described before, the stabilized Collaborome led to a maximized SCFA production (acetate/propionate/butyrate ratio was around 14/12/74) two days earlier as compared to the same set of species in the assembly strategy and a 25% higher butyrate production.

Example 2: In Vitro Experiments 2.1 Effect of Adding the Functional Composition to Complex Microbial Gut Communities This experiment demonstrates that the functional composition is active when inoculated in a mixed microbial gut community, where there is a strong competition for colonic substrates with members of this complex intestinal community that is estimated to consist of 500 to 1000 microbial species. To address this issue, an experiment was performed in small incubation bottles using the composition, containing *Lactobacillus plantarum, Faecalibacterium prausnitzii, Butyricicoccus pullicaecorum, Roseburia inulinivorans, Roseburia hominis, Akkermansia muciniphila* and *Anaerostipes caccae* and produced through the Collaborome strategy from Example 1.3. An increasing concentration of the pre-adapted composition (0%, 4% and 20%) was washed in PBS and added to three different media:

1) Sterile basal medium [2 g/L pepton, 2 g/L yeast extract, 2 mL/L TWEEN® 80, 10 µL/L, vitamin K1, 500 mg/L L-cysteine HCl, 100 mg/L NaCl, 40 mg/L $K_2HPO_4$, 40 mg/L $KH_2PO_4$, 10 mg/L $MgSO_4.7H_2O$, 6.7 mg/L $CaCl_2.2H_2O$, 1.5 mg/L resazurin, 50 mg/L hemin (50 mg/L)—pH 5.5]+starch 6 g/L;
2) Basal medium+20% fecal slurry (prepared as described in De Boever et al., 2000);
3) Basal medium+20% SHIME® colon suspension, containing the complete microbiota.

Figure 7:
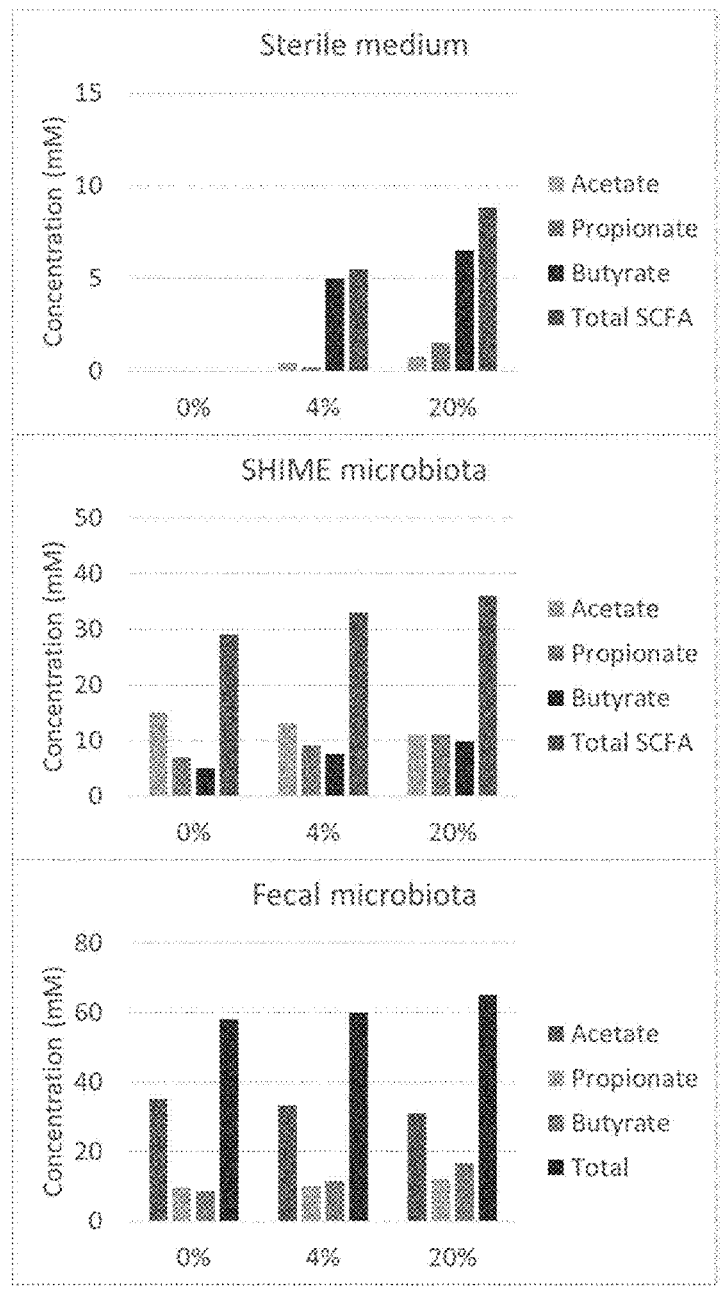
FIG. 7: Production (mM) of acetate, propionate, butyrate and total short-chain fatty acids (SCFA) in 24-hour incubations with (i) sterile basal medium (top panel), or sterile medium supplied with (ii) microbiota derived from a SHIME® colon region (middle panel) or (iii) fecal microbiota (lower panel). Different treatments with the composition, produced through the "Collaborome" strategy, were applied ranging from 0% to 4% and 20% of the total incubation volume.

The increasing concentration of the pre-adapted butyrate-producing consortium from 0% to 4% and 20% resulted in a proportional increase of absolute butyrate levels (FIG. 7). This was not only observed in sterile medium, but also for media supplemented with a mixed microbiota derived from both a fecal sample or a SHIME® colon region. This experiment thus demonstrates that composition is not only active when present in a non-competing colonic environment, but that it also results in higher butyrate levels when administered to a mixed microbiota where many gut microbes are competing for the same nutrients. Furthermore, not only butyrate production increased, but also propionate production strongly increased. The combination of these increases and the decrease of acetate in the incubation stipulates that the composition can modulate general microbial fermentation profiles into a more health-beneficial profile.

2.2 Efficiency of the Functional Composition to Restore the Metabolic Functions of an Antibiotic-Induced Dysbiosed Gut Microbial Community The use of antibiotics is believed to cause major disruptions of the gut microbiota community. It has been shown that a dysbiosed microbial composition is more susceptible to infections by pathogens. Furthermore, a number of gastrointestinal diseases have been correlated with a dysbiosed microbial composition, such as inflammatory bowel diseases, underlining the importance of a healthy gut microbiome. Recovery of the taxonomic composition and especially functionality after long-term antibiotic intake usually takes three months to reach the pre-treatment state, a healthy gut microbial community (Panda et al., 2014). A decrease in the recovery time after exposure to antibiotic therapy could thus reduce the risk of severe infections and promote host health in general. In that respect, the observed functional activity of the selected composition could be a promising strategy to enhance restoration of microbial communities upon antibiotics-induced dysbiosis and reduce infection risks.

In this example, antibiotics-induced dysbiosis was modeled in the in vitro SHIME® model by dosing the appropriate antibiotics. The aim of this experiment was to evaluate the recovery of the typical "healthy" metabolite profiles in the simulated intestinal colon environments upon administration of the functional composition. Furthermore, the experiment aimed to differentiate the effectivity of the composition, when either produced through the "Assembly" strategy or the "Collaborome" strategy (see Example 1.3). The experiment was again performed with the composition, containing *Lactobacillus plantarum, Faecalibacterium prausnitzii , Butyricicoccus pullicaecorum, Roseburia inulinivorans, Roseburia hominis, Akkermansia muciniphila* and *Anaerostipes caccae*. To better mimic the complete functionality profile of the intestinal microbiome, the composition was in this specific experiment further supplemented with *E. coli, Enterococcus faecium, Lactobacillus mucosae, Bifidobacterium adolescentis, Bifidobacterium longum, Bacteroides thetaiotaomicron* and *Bacteroides vulgatus*.

Figure 8:
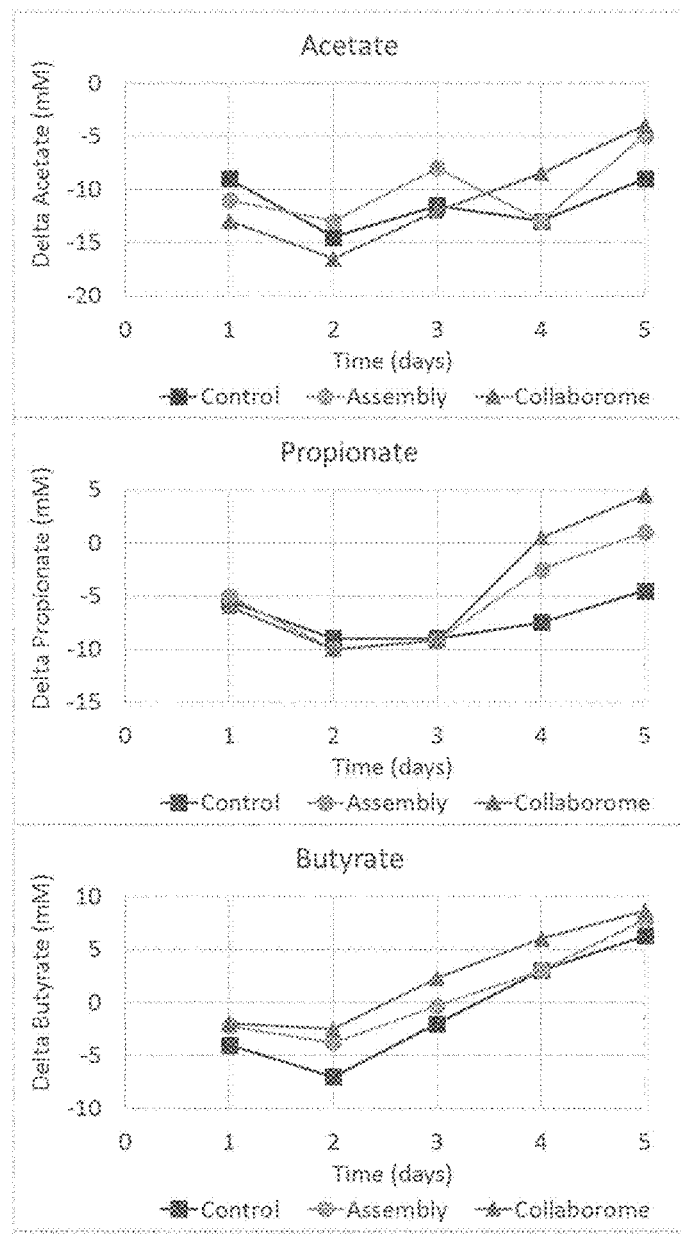
FIG. 8: Evolution of levels (mM) of acetate (top panel), propionate (middle panel) and butyrate (lower panel) in an antibiotic recovery experiment in the M-SHIME®. Upon dysbiosis induction of the SHIME®-derived colon microbiota through administration of a cocktail of antibiotics (40/40/10 mg/L of amoxicillin/ciprofloxacin/tetracycline, respectively), the dysbiosed microbiota was treated for five days with the composition, produced either through the "Assembly" strategy or the "Collaborome" strategy (day 1=start of administration of the composition). The results are expressed as the delta of SCFA levels in the SHIME® at each time point vs. the values before antibiotic administration.

In practice, SHIME® vessels (pH 6.15-6.40) were inoculated with fecal material and allowed to stabilize for fourteen days (M-SHIME® setup—Van den Abbeele et al., 2012). After a control period of two weeks, the SHIME®-derived colon microbiota was treated with a cocktail of antibiotics (40/40/10 mg/L of amoxicillin/ciprofloxacin/tetracycline, respectively) to induce dysbiosis. One day later, the dysbiosed microbiota was treated for five days with the functional composition, produced either through the "Assembly" strategy or the "Collaborome" strategy. Endpoint of the study was to evaluate the recovery of the typical "healthy" SCFA metabolite profiles in the simulated intestinal colon environments. A control SHIME® vessel was included to simulate spontaneous recovery of the metabolic activity of the gut community after antibiotic exposure, without administration of the composition. The results are expressed as the delta of SCFA levels in the SHIME® at each time point vs. the values before antibiotic administration (FIG. 8).

Upon antibiotic treatment of the SHIME® vessels, a significant drop in acetate, propionate and butyrate production was observed. This finding confirms the disruption of the gut microbial community. Recovery of the metabolite profile (in terms of SCFA production) to the pre-treatment state is shown in FIG. 8 as the evolution of acetate, propionate and butyrate over a 5-day period. This shows that recovery of the functionality was slow in the control situation (no administration of composition) and no full recovery could be observed for acetate and propionate within five days. Interestingly, treatment with the composition resulted in a faster recovery as compared to the control condition for all three SCFA. Furthermore, while the composition of the Assembly strategy induced full recovery of propionate and butyrate after five days and three days, respectively, the composition of the Collaborome strategy induced a faster recovery as opposed to the Assembly strategy with full recovery of propionate and butyrate after four days and 2.5 days, respectively. Finally, the Collaborome strategy also resulted in an increased final activity with increased propionate and butyrate levels as opposed to the Assembly strategy. These results emphasize the potential of the composition for the recovery of antibiotic-mediated microbial dysbiosis. Moreover, this finding clearly demonstrates that the preadaptation through the Collaborome strategy results in a more efficient recovery of microbial SCFA production after antibiotic exposure as compared to the Assembly strategy.

2.3 Efficiency of the Functional Composition to Restore the Metabolic Functions of a Dysbiosed Gut Microbial Community in Inflammatory Bowel Diseases Inflammatory Bowel Diseases (IBD) have been associated with impaired host-microbe interactions, which is related, at least partially, to a state of gut microbiota dysbiosis. The latter, for instance, includes a lower abundance of butyryl CoA:acetate CoA transferase and propionate kinase (Vermeiren et al., FEMS 2011), which, in turn, negatively affects the production of a balanced SCFA production capacity. Given the important effects of SCFA on normal intestinal development and maintenance, restoration of the microbiota composition and functionality in terms of SCFA production can positively impact IBD-associated symptoms. In that respect, the observed functional activity of the selected composition could be a promising strategy to enhance restoration of microbial communities in IBD dysbiosis as a basis for restoration and maintenance of a healthy gut barrier.

In this example, IBD-associated dysbiosis was modeled in the in vitro M-SHIMS® model, as described before (Vigsnaes et al. 2013). The aim of this experiment was to evaluate the recovery of the microbiota in terms of SCFA profiles in the simulated intestinal colon environment upon administration of the functional composition. Furthermore, the experiment aimed to differentiate the effectivity of the composition, when either produced through the "Assembly" strategy or the "Collaborome" strategy (see Example 1.3). The experiment was again performed with the composition, containing *Lactobacillus plantarum, Faecalibacterium prausnitzii, Butyricicoccus pullicaecorum, Roseburia inulinivorans, Roseburia hominis, Akkermansia muciniphila* and *Anaerostipes caccae*.

In practice, SHIMS® vessels (pH 6.15-6.40) were inoculated with fecal material from an Ulcerative Colitis patient (M-SHIME® setup—Van den Abbeele et al., 2012). Simultaneously, a single dose of the functional composition, produced either through the "Assembly" strategy or the "Collaborome" strategy, was added to the colon region to simulate administration. A third experiment ran in parallel as control experiment without administration of the composition. Production of acetate, propionate and butyrate was followed one and two days after administration of the composition.

Figure 9:
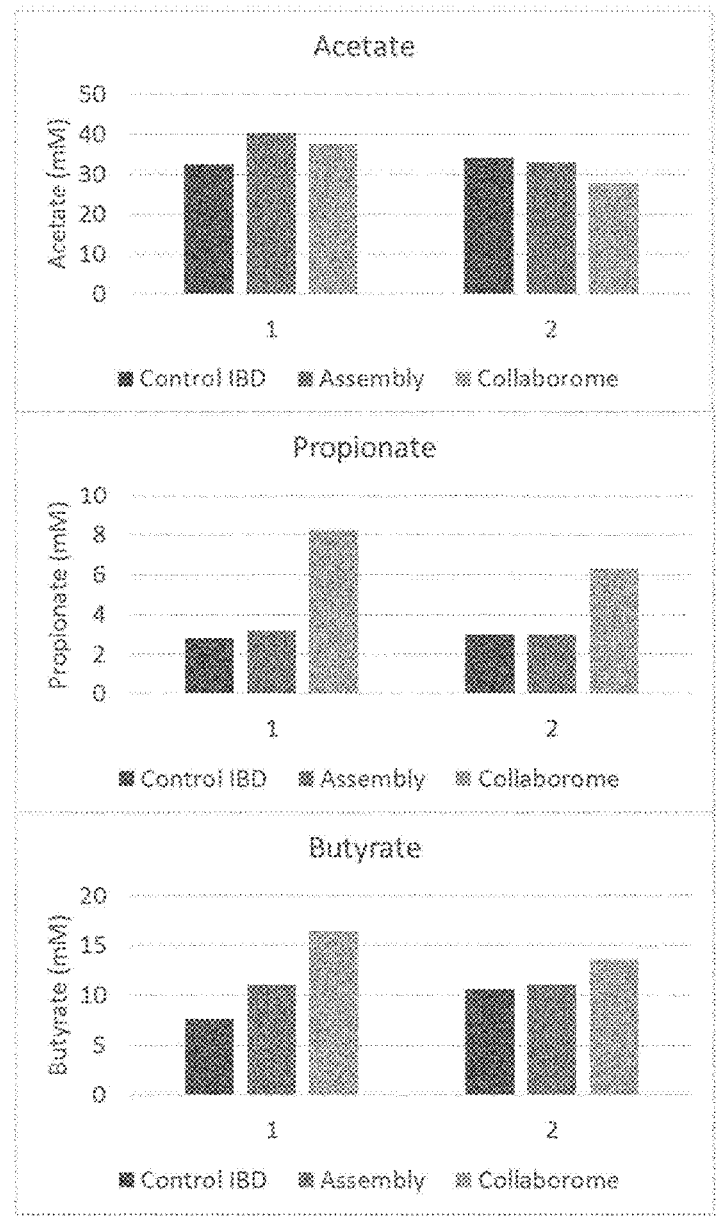
FIG. 9: Levels (mM) of acetate (top panel), propionate (middle panel) and butyrate (lower panel) in an IBD-associated dysbiosis recovery experiment in the M-SHIME®. Three independent SHIME® colon vessels were inoculated with fecal material from an Ulcerative Colitis patient. Simultaneously, a single dose of the composition, produced either through the "Assembly" strategy or the "Collaborome" strategy, was added to a respective SHIME® colon vessel. A third experiment ran in parallel as control experiment without administration of the composition. Production of acetate, propionate and butyrate was followed one and two days after administration of the composition.

The results are presented in FIG. 9: administration of the composition, produced in the Assembly strategy, resulted in an increased SCFA production (mainly acetate and butyrate) on day 1, yet this effect was no longer apparent on day 2. This indicates that the composition is functionally active in the IBD microbiome environment. Interestingly, the effect on propionate and butyrate production was much more pronounced upon administration of the composition of the Collaborome strategy, with a four-fold and three-fold increase in propionate and butyrate production, respectively, as opposed to the IBD control. In contrast with the composition of the Assembly strategy, the effect was still pronounced on day 2 and coincided with a lower acetate production (indication of increased cross-feeding and, therefore, improved networking). These results emphasize the potential of the composition for the recovery of IBD-associated microbial dysbiosis. Moreover, this finding clearly demonstrates that the preadaptation through the Collaborome strategy results in a more efficient recovery of microbial SCFA production under IBD conditions as compared to the Assembly strategy.

2.4 Efficiency of the Functional Composition to Inhibit Growth of Vegetative *Clostridium Difficile* in an In Vitro Simulation Assay In this example, a *Clostridium difficile* challenge test was performed aiming to evaluate whether the functional composition is not only functionally active under intestinal conditions, yet can also protect the intestinal environment against infections. In such challenge test, the composition is challenged with vegetative *Clostridium difficile* (Cdif) cells to assess its capacity to inhibit growth of Cdif under simulated gastro-intestinal conditions. Furthermore, the experiment aimed to differentiate the effectivity of the composition, when either produced through the "Assembly" strategy or the "Collaborome" strategy (see Example 1.3). The experiment was again performed with the composition, containing *Lactobacillus plantarum, Faecalibacterium prausnitzii, Butyricicoccus pullicaecorum, Roseburia inulinivorans, Roseburia hominis, Akkermansia muciniphila* and *Anaerostipes caccae*.

In practice, a glycerol stock of *Clostridium difficile* (LMG $21717^T$) was thawed and inoculated in a bottle containing Reinforced Clostridial Medium (RCM) broth that was flushed with nitrogen to ensure anaerobic conditions. The bottle was incubated in a shaking incubator (90 rpm) for 24 hours and 10% of the grown culture was again inoculated in RCM broth. After 24 hours of growth, the homogenized *C. difficile* culture was aliquoted (in triplicate) in bottles (10% v:v) containing:

1) Basal medium (blank);
2) Basal medium containing the composition of the Assembly strategy;
3) Basal medium containing composition of the Collaborome strategy;
4) Basal medium containing SHIME® colon suspension.

Bottles were incubated at 37° C. in a shaking incubator (90 rpm). At regular time points, a sample was collected and immediately frozen at −80° C. before quantifying *C. difficile* by means of a qPCR assay based on the detection and quantification of the triose phosphate isomerase gene. For this purpose, genomic DNA was extracted according to Boon et al. (2003). The amplification reaction included forward and reverse oligonucleotide: 5'-TATGGAC-TATGTTGTAATAGGAC-3' (forward) (SEQ ID NO:8) and 5'-CATAATATTGGGTCTATTCCTAC-3' (reverse) (SEQ ID NO:9). Absolute quantification of the PCR product was obtained by creating a standard curve.

In this controlled in vitro simulation assay, growth of *C. difficile* was observed in the basal medium after 48 hours of incubation, confirming the validity of the blank in the in vitro simulation assay. The SHIME® colon suspension (as simulation of an actual fecal transplant) showed the highest *C. difficile* growth inhibition after 48 hours of incubation (i.e., 58%). Interestingly, a similar result was obtained for the composition of the Collaborome strategy, showing approximately 53% of *C. difficile* growth inhibition. The lowest effect was observed when the composition of the Assembly strategy was added (i.e., 23% of growth inhibition). This experiment clearly demonstrates that *C. difficile* is significantly inhibited in its growth by the composition and that this inhibition is most pronounced in case of preadaptation of the composition through the Collaborome strategy.

2.5 Effect of the Functional Composition on Host Biomarkers of Gut Barrier Functioning and Intestinal Immunity Examples 2.1 to 2.3 showed that the composition is functionally active under complex intestinal conditions and can restore intestinal metabolite profiles, with highest activity in the case of the production through the Collaborome strategy. This may, in turn, beneficially influence the intestinal epithelium and thereby gut barrier functioning and local immunity.

To evaluate that possibility, this example describes the combination of samples collected from the previous experiments on an established co-culture cell model of enterocytes (Caco-2 cells) and macrophages (THP1) (Possemiers et al. 2013). In this model, stimulation of THP1 cells with LPS results in increased production of pro-inflammatory cytokines, which, in turn, tends to disrupt the enterocyte layer creating a so-called "leaky gut" condition. The effect on the "leaky gut" is measured by assessing the effect of the transepithelial electrical resistance (TEER) [measurement for gut barrier efficiency] and inflammatory cytokine production, as compared to a control condition.

In practice, samples collected on day 1 from the M-SHIME® experiment from Example 2.3 were combined with the co-culture leaky gut model.

2.6 Impact of Variations in Strain Identity on Functional Activity of the Composition To assess whether the surprising synergistic effect between the seven isolates in the composition is strain specific or can also be reached with other strains of the same species, an additional experiment was performed. In this example, two different compositions are produced through the "Collaborome" strategy (see Example 1.3). While composition 1 contains the specific isolates described in Example 1.2, composition 2 is composed of strains from the same species obtained from culture collections:

Composition 1: *Faecalibacterium prausnitzii* LMG P-29362, *Butyricicoccus pullicaecorum* LMG P-29360, *Roseburia inulinivorans* LMG P-29365, *Roseburia hominis* LMG P-29364, *Akkermansia muciniphila* LMG P-29361, *Lactobacillus plantarum* LMG P-29366 and *Anaerostipes caccae* LMG P-29359

Composition 2: *Lactobacillus plantarum* ZJ316, *Faecalibacterium prausnitzii* (DSMZ 17677), *Butyricicoccus pullicaecorum* (LMG 24109), *Roseburia inulinivorans* (DSMZ 16841), *Roseburia hominis* (DSMZ 16839), *Akkermansia muciniphila* (DSMZ 22959) and *Anaerostipes caccae* (DSMZ 14662)

In practice, the selected species were retrieved from their glycerol stocks and grown under their respective optimal growth conditions to obtain homogeneous suspensions of the bacterial strains. Then, the strains were mixed into Composition 1 and Composition 2, respectively, and each inoculated in triplicate in a SHIME® setup (Van den Abbeele et al., 2010) consisting of a single colon region at a pH of 6.15-6.4. Butyrate production profiles were followed up for a period of fourteen days.

Interestingly, the dynamics in butyrate production were highly similar for both Compositions, with initial strong fluctuations, followed by stabilization of butyrate levels after approximately six days. At the end of the experiment (d14), butyrate levels for Composition 1 reached 19.3 mM, while levels for Composition 2 were 18.8 mM. This shows that the synergistic effect observed in the composition from Example 1.2 could be replicated by using different strains obtained from the same species.

Example 3: In Vivo Experiments 3.1 Mouse Model of Antibiotic-Induced Gastrointestinal Microbiota Disruption The goal of the experiment in this example was to assess whether the functional composition can also in an in vivo setting restore the metabolic capacity of the gut microbiome after antibiotic-induced dysbiosis.

In this example, the composition, containing *Lactobacillus plantarum*, *Faecalibacterium prausnitzii*, *Butyricicoccus pullicaecorum*, *Roseburia inulinivorans*, *Roseburia hominis*, *Akkermansia muciniphila* and *Anaerostipes caccae*, was used and produced via the "Collaborome" strategy of Example 1.3. Furthermore, to evaluate the need for more complete mimicking of the complete functionality profile of the intestinal microbiome, an extra experiment was performed in which the composition was further supplemented with *Escherichia coli*, *Enterococcus faecium*, *Lactobacillus mucosae*, *Bifidobacterium adolescentis*, *Bifidobacterium longum*, *Bacteroides thetaiotaomicron* and *Bacteroides vulgatus* (referred to as "extended composition").

In practice, the "composition" and "extended composition" were prepared fresh according to the Collaborome strategy, washed twice in PBS (in an anaerobic chamber to ensure anaerobic conditions), concentrated in 100 μL and administered to the mice via oral gavage as soon as possible. Mice (C57/BL6) of at least five weeks old were purchased, kept under pathogen-free conditions and fed a standard diet. Mouse experiments were performed in accordance with protocols approved by the Ethics Committee of Animal Trials of Ghent University, Belgium. To induce antibiotic-induced dysbiosis, the antibiotic clindamycin was dosed to the drinking water at a concentration of 250 mg/L. After five days of antibiotic treatment, the stomach content of the mice was neutralized with $NaHCO_3$ after which the mice (ten mice per group) are orally gavaged for five consecutive days with:

1) the composition in saline solution;
2) the extended composition in saline solution and
3) saline solution (control).

A conventional group (without antibiotic treatment but treated with saline solution) is included as control to exclude variability arising from the gavage procedure. During the experiment, fecal samples (approximately 100 mg/mouse) were collected and stored at −80° C. for future analyses.

Figure 10:
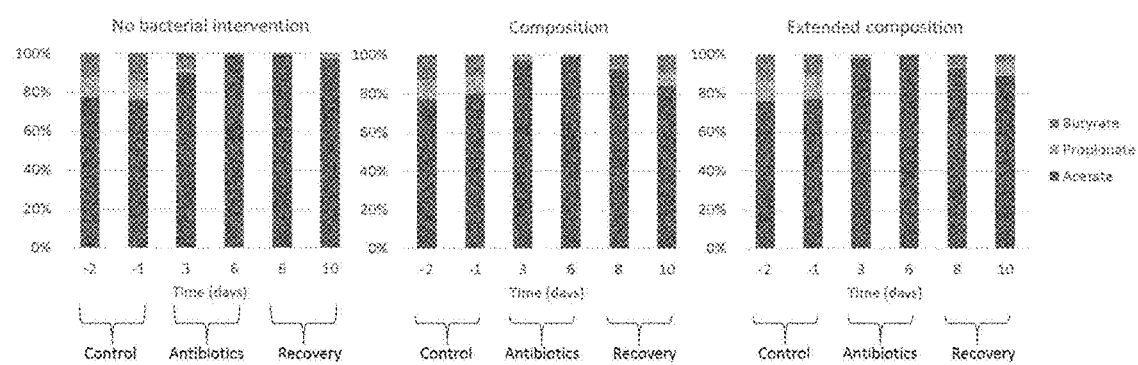
FIG. 10: Evolution of levels (mol %) of acetate, propionate and butyrate in an antibiotic recovery experiment in C57/BL6 mice. After a control period in which the mice were fed a standard diet, gut microbiota dysbiosis was induced by adding clindamycin (250 mg/L) to the drinking water for five days. After this, the mice (n=10/group) were orally gavaged for five days with either saline solution (no bacterial intervention control; left panel), the composition, produced through the "Collaborome" strategy (middle panel) or the extended composition, produced through the "Collaborome" strategy (right panel). Mice fecal samples obtained from the same intervention group were pooled and levels of acetate, propionate and butyrate were quantified.

The SCFA profiles, obtained from pooled mice fecal samples originating from the same groups, demonstrate that five days of antibiotic treatment significantly reduce butyrate and propionate production up to the extent that only acetate remained (FIG. 10). As it is shown in FIG. 10, spontaneous recovery of the metabolic functions is slow and only started about five days (d 10) after the last antibiotic treatment, although the molar ratios of the three major SCFA (acetate, propionate and butyrate) did not yet return to the pre-antibiotic state. When mice were, however, treated with either the composition or extended composition of the Collaborome strategy, recovery of butyrate metabolism already started approximately three days (d8) after antibiotic treatment. Furthermore, the metabolic activity of the mice treated with both compositions showed almost complete recovery five days after the last dose of antibiotics (d10), with good production of both propionate and butyrate. The extended composition contained a higher diversity of acetate and propionate producers as compared to the composition, which is also reflected by the slightly different fermentation profile at d10 of the experiment. In conclusion, this example provides an in vivo confirmation that the functional composition is effective in obtaining a faster and more potent recovery of intestinal metabolic profiles upon antibiotic-induced dysbiosis. Furthermore variations in the exact species combinations in the composition allows tuning the end result into specific metabolic profiles.

3.2 TNBS Mouse Model for Inflammation

The TNBS (2,4,6-trinitrobenzenesulfonic acid) model is a commonly used model for colitis that mimics some of the features of Crohn's disease (Scheiffele et al. 2001), including weight loss, bloody diarrhea and intestinal wall thickening. On histopathology, TNBS causes patchy transmural inflammation of the gut with the formation of deep ulcers, classical features found in patients with CD. This makes the TNBS model a good candidate for in vivo evaluation of the capacity of the functional composition to prevent and/or restore damage to the intestinal mucosa in IBD and to assist in maintaining/developing a healthy gut barrier.

In this example, the composition, containing *Lactobacillus plantarum, Faecalibacterium prausnitzii, Butyricicoccus pullicaecorum, Roseburia inulinivorans, Roseburia hominis, Akkermansia muciniphila* and *Anaerostipes caccae* was used to evaluate the beneficial effects upon evaluation in the TNBS model. Furthermore, the experiment aimed to differentiate the effectivity of the composition, when either produced through the "Assembly" strategy or the "Collaborome" strategy (see Example 1.3). Colitis was evoked in the animals by rectal instillation of TNBS, a mucosal sensitizing agent diluted in ethanol. The administration of ethanol is a prerequisite to break the colonic mucosal barrier to allow penetration of TNBS into the lamina propria. TNBS haptenizes the localized colonic and gut microbial proteins to become immunogenic, thereby triggering the host innate and adaptive immune responses.

In practice, eight- to ten-week-old male C57BL6/J mice were housed in a temperature-controlled room at 20° C. with a 12:12-hour light-dark cycle. The animals had free access to water and to a commercial chow. Mice were randomized among cages to avoid cage effects. After one week of acclimatization, the experiment was started. Each group (n=9/group) was treated for five consecutive days by means of oral gavage. Preventive dosing of all treatments started one day before the administration of 2 mg TNBS/50% EtOH rectally and lasted for four days after TNBS administration before mice were sacrificed. The following treatments were included:
1) TNBS+ the composition of the Assembly strategy in saline solution;
2) TNBS+ the composition of the Collaborome strategy in saline solution and
3) TNBS+ saline solution (control).

A conventional group (without TNBS treatment but treated with saline solution) is included as control to exclude variability arising from the gavage procedure. As study endpoint, Disease Activity was monitored daily (before the daily treatment) by measuring body weight, fecal blood loss (ColoScreen) and general appearance.

Figure 11:
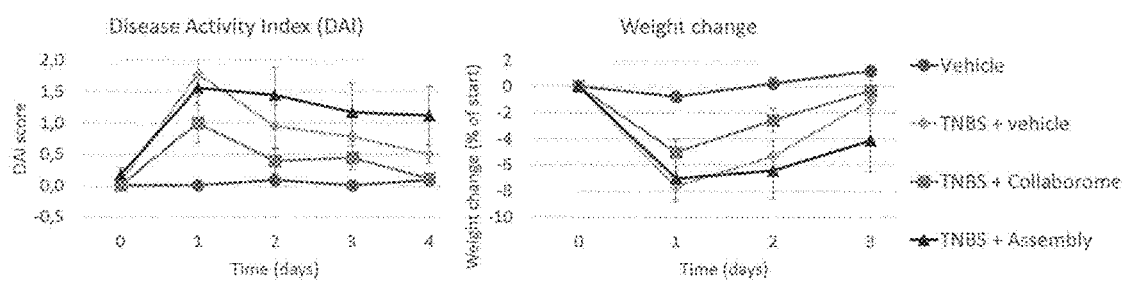
FIG. 11: Evolution of the Disease Activity Index (DAI) and weight change in a TNBS-induced colitis experiment in C57/BL6 mice. After a one-week acclimatization period in which the mice were fed a standard diet, the experiment was started. Each group (n=9/group) was treated for five consecutive days by means of oral gavage. Preventive dosing of all treatments started one day before the rectal administration of 2 mg TNBS/50% EtOH and lasted for four days after TNBS administration, before mice were sacrificed. The following treatments were included: TNBS+ saline solution (vehicle TNBS control); TNBS+ composition, produced through the "Assembly" strategy, and TNBS+ composition, produced through the "Collaborome" strategy. A conventional group (without TNBS treatment but treated with saline solution) was included as vehicle control.

The results of this example are presented in FIG. 11. No effects on weight nor Disease Activity were observed for the Vehicle (saline) control group without TNBS, while the control group that received TNBS showed an immediate weight loss on d1 of 8% and a strong increase in Disease Activity. Both weight loss and Disease activity were partially restored by the end of the study. Interestingly, a potent protective effect of the composition was observed on both weight loss and Disease Activity, yet the extent of this protective effect depended on the production strategy of the composition. While an initial mild protection was observed on d1 for the Assembly strategy as shown to be lower weight loss and Disease Activity, this protective effect was no longer observed on the next study days. In contrast, the administration of the composition produced through the Collaborome strategy led to a potent preventive effect toward weight loss and Disease Activity on d1, as compared to the TNBS control, and a faster and complete restoration by the end of the study, as shown by the return of the disease activity to the level of the Vehicle control. In conclusion, this example provides an in vivo confirmation that the functional composition is effective in obtaining a stronger prevention of, and faster and more potent recovery from, intestinal inflammation and Disease Activity upon TNBS-induced colitis induction. Moreover, this finding clearly demonstrates that the preadaptation through the Collaborome strategy results in a more efficient activity as compared to the Assembly strategy.

3.3 DSS Mouse Model for Inflammation

The chronic DSS model is a commonly used model for colitis that mimics some of the features of Crohn's disease, including weight loss and bloody diarrhea. On histopathology, chronic DSS administration causes inflammation of the gut with typical architectural changes such as crypt distortion, (sub)mucosal infiltration of inflammatory cells and fibrosis, features found in patients with CD. This makes the DSS model a good candidate for in vivo evaluation of the capacity of the functional composition to prevent and/or restore damage to the intestinal mucosa in IBD and to assist in maintaining/developing a healthy gut barrier.

In this example, the composition, containing *Lactobacillus plantarum, Faecalibacterium prausnitzii, Butyricicoccus pullicaecorum, Roseburia inulinivorans, Roseburia hominis, Akkermansia muciniphila* and *Anaerostipes caccae*, and produced through the "Collaborome" strategy (see Example 1.3), is used to evaluate the beneficial effects upon evaluation in the chronic DSS model. Colitis is evoked in the animals by repeated administration of DSS in the drinking water (0.25% challenge). The experiment is performed over a total of eight weeks, with three cycles of DSS administration and recovery.

In practice, six-week-old male C57BL6/J mice are housed in a temperature-controlled room at 20° C. with a 12:12-hour light-dark cycle. The animals have free access to water and to a commercial chow. Mice are randomized among cages to avoid cage effects. After one week of acclimatization, the experiment is started. Each group (n=10/group) is treated three times per week for eight consecutive weeks, by means of oral gavage. Preventive dosing of all treatments starts one week before the first DSS cycle. The first DSS cycle starts on week 2 and includes one week of DSS administration (0.25% in drinking water) followed by two weeks of recovery. This first cycle is followed by an identical second DSS cycle. The third DSS cycle consists of one week of DSS administration followed by one week of recovery, after which the animals are sacrificed. The following treatments are included:
1) non-DSS control
2) DSS+ the composition of the Collaborome strategy in saline solution (three times/week) and
3) DSS+ saline solution (DSS control).

Figure 12:
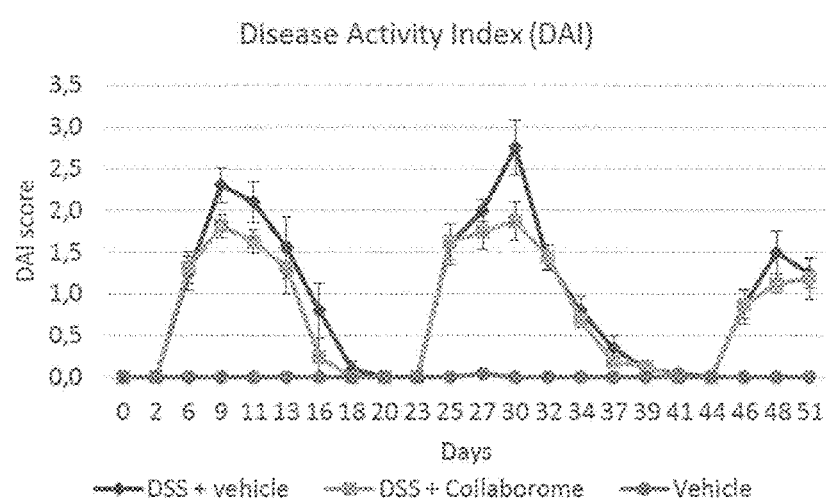
FIG. 12: Evolution of the Disease Activity Index (DAI) in a DSS-induced chronic colitis experiment in C57/BL6 mice. After a one-week acclimatization period in which the mice were fed a standard diet, the experiment was started. Each group (n=10/group) was treated three times per week for eight consecutive weeks, by means of oral gavage. Preventive dosing of all treatments started one week before the first DSS cycle. The first DSS cycle started on week 2 and included one week of DSS administration (0.25% in drinking water) followed by two weeks of recovery. This first cycle was followed by an identical second DSS cycle. The third DSS cycle consisted of one week of DSS administration followed by one week of recovery, after which the animals were sacrificed. The following treatments were included: DSS+ saline solution (vehicle DSS control); DSS+ composition, produced through the "Collaborome" strategy. A conventional group (without DSS treatment but treated with saline solution) was included as vehicle control.

As study endpoint, the Disease Activity Index (DAI) was monitored during each DSS cycle, three times per week (before the daily treatment) by monitoring body weight, fecal blood loss (ColoScreen) and general appearance. As shown in FIG. 12, no effects on DAI were observed for the Vehicle (saline) control group without DSS, while the control group that received DSS showed a strong increase in DAI at each administration cycle. Interestingly, a potent protective effect (approximately 25% lower DAI at each cycle) of the composition was observed on Disease Activity. This further demonstrates that the functional composition is effective in obtaining a strong protective effect from intestinal inflammation and Disease Activity upon DSS-induced colitis induction.

3.4 Mucositis Model

Mucositis is a clinical term used to describe damage to mucous membranes after anticancer therapies. It occurs throughout the entire gastrointestinal tract (GT) (including the mouth) and genito-urinary tract, and to a lesser extent in other mucosal surfaces. Its severity and duration varies with the dose and the type of drug used. The importance of mucositis is that it limits the dose of chemotherapy. The GI crypt epithelium is particularly vulnerable to chemotherapeutic toxicity, with symptoms including nausea and vomiting, abdominal pain, distension, and diarrhea due to direct effects of the cytotoxics on the mucosa. The 5-fluorouracyl (5FU)-induced gut mucositis rat model was established by Keefe et al. for assessment of the effects of chemotherapy on the GI tract and it is now one of the most extensively used models to investigate chemotherapy-induced mucositis in rats (Keefe 2004).

In this example, the composition, comprising *Lactobacillus plantarum, Faecalibacterium prausnitzii, Butyricicoccus pullicaecorum, Roseburia inulinivorans, Akkermansia muciniphila* and *Anaerostipes caccae*, was used as the basis for the experiment and produced via the "Collaborome" strategy of Example 1.3. Mucositis is induced by means of a single intraperitoneal dose of 5FU.

In practice, a total of 30 rats were randomly assigned to either a control or experimental group according to a specific time point. All rats in the experimental groups received a single intraperitoneal dose of 5FU (150 mg 5FU/kg BW). Rats in the control groups received treatment with the solvent vehicle (dimethylsulphoxide). Subsequent to administration of the chemotherapy drugs, study endpoints such as mortality, diarrhea, and general clinical condition were assessed four times per 24-hour period. Subgroups of the rats were killed by exsanguination and cervical dislocation at 24, 48, and 72 hours following administration of the drug. Primary endpoints of interest were evolution of weight, diarrhea and general wellbeing (sickness score). Secondary endpoints included histology of intestinal samples and stool and gut mucosal microbiota analysis.

To assess the effect of the composition on prevention or reducing the evaluated symptoms, part of the rats were administered for eight consecutive days with the composition by means of oral gavage. Preventive dosing started five days before the administration of 5FU and lasted for three days after 5FU administration or until rats were sacrificed. Control animals did not receive the composition.

REFERENCES

Bahaka et al. 1993—Phenotypic and genomic analyses of human strains belonging or related to *Bifidobacterium longum, Bifidobacterium infantis*, and *Bifidobacterium breve.—Int. J. Syst. Evol. Microbiol.* 43:565-573.

Barcenilla et al. 2000—Phylogenetic relationships of butyrate-producing bacteria from the human gut—*Appl. Environ. Microbiol.* 66:1654-1661.

Barnett et al. 2012—The interactions between endogenous bacteria, dietary components and the mucus layer of the large bowel.—*Food Funct.* 3:690-9.

Becker et al. 2011—Human intestinal microbiota: characterization of a simplified and stable gnotobiotic rat model—*Gut Microbes* 2:25-33.

Boon et al. 2003—Bioaugmentation as a tool to protect the structure and function of an activated-sludge microbial community against a 3-chloroaniline shock load—*Appl. Environ. Microbiol.* 69:1511-1520.

Brandl et al. 2008—Vancomycin-resistant enterococci exploit antibiotic-induced innate immune deficits—*Nature* 455:804-7.

Cénit et al. 2014—Rapidly expanding knowledge on the role of the gut microbiome in health and disease—*Biochim. Biophys. Acta.* 1842:1984-1992.

Clemente et al. 2012—The impact of the gut microbiota on human health: an integrative view—*Cell* 148:1258-70.

Cummings & Macfarlane, 1997—Role of intestinal bacteria in nutrient metabolism—*J. Parenter. Enteral. Nutr.* 21:357-65.

Derrien et al. 2004—Akkermansia muciniphila gen. nov., sp. nov., a human intestinal mucin-degrading bacterium—*Int. J. Syst. Evol. Microbiol.* 54:1469-1476.

De Vrieze 2013—Medical research. The promise of poop—*Science* 341:954-7.

Duncan et al. (2002)—Growth requirements and fermentation products of *Fusobacterium prausnitzii*, and a proposal to reclassify it as *Faecalibacterium prausnitzii* gen. nov., comb. nov. —*Int. J. Syst. Evol. Microbiol.* 52:2141-2146.

Duncan et al. (2006)—Proposal of *Roseburia faecis* sp. nov., *Roseburia hominis* sp. nov. and *Roseburia inulinivorans* sp. nov., based on isolates from human faeces—*Int. J. Syst. Evol. Microbiol.* 56:2437-2441.

Eeckhaut et al. (2008)—*Butyricicoccus pullicaecorum* gen. nov., sp. nov., an anaerobic, butyrate-producing bacterium isolated from the caecal content of a broiler chicken—*Int. J. Syst. Evol. Microbiol.* 58:2799-2802.

Fuller & Gibson, 1997—Modification of the intestinal microflora using probiotics and prebiotics—*Scand. J. Gastroenterol. Suppl.* 222:28-31.

Hartemink et al. 1996—Raffinose-Bifidobacterium (RB) agar, a new selective medium for bifidobacteria—*J. Microbiol. Methods* 27:33-43.

Hartemink et al. 1997—LAMVAB—A new selective medium for the isolation of lactobacilli from faeces—*J. Microbiol. Methods* 29:77-84.

Iannitti and Palmieri, 2010—Therapeutical use of probiotic formulations in clinical practice—*Clin. Nutr.* 29:701-25.

Le Bon et al. 2010—Influence of probiotics on gut health in the weaned pig—*Livestock Sci.* 133:179-181.

Livingston et al. 1978—New medium for selection and presumptive identification of the *Bacteroides fragilis* group—*J. Clin. Microbiol.* 7:448-453.

Keefe 2004—Gastrointestinal mucositis: a new biological model—*Supp. Care Canc.* 12:6-9.

Khoruts et al. 2010—Changes in the composition of the human fecal microbiome after bacteriotherapy for recurrent *Clostridium difficile*-associated diarrhea—*J. Clin. Gastroenterol.* 44:3 54-60.

Kinross et al. 2011—Gut microbiome-host interactions in health and disease—*Genome Med.* 3:14.

Macfarlane & Macfarlane, 1997—Human colonic microbiota: ecology, physiology and metabolic potential of intestinal bacteria—*Scand. J. Gastroenterol.* 32:3-9.

Newton et al. 1998—Growth of a human intestinal Desulfovibrio desulfuricans in continuous cultures containing defined populations of saccharolytic and amino acid fermenting bacteria—*J. Appl. Microbiol.* 85:372-380.

Panda et al. 2014—Short-Term Effect of Antibiotics on Human Gut Microbiota—*PloS One* 9:e95476.

Petrof et al. 2013—Stool substitute transplant therapy for the eradication of *Clostridium difficile* infection: "RePOOPulating" the gut—*Microbiome* 1:3-10.

Possemiers et al. 2004—PCR-DGGE-based quantification of stability of the microbial community in a simulator of the human intestinal microbial ecosystem—*FEMS Microbiol. Ecol.* 49:495-507.

Possemiers et al. 2013—A dried yeast fermentate selectively modulates both the luminal and mucosal gut microbiota, enhances butyrate production and protects against inflammation, as studied in an integrated in vitro approach—*J. Agric. Food Chem.* 61:9380-9392.

Rath et al. 1999—Differential induction of colitis and gastritis in HLA-B27 transgenic rats selectively colonized with *Bacteroides vulgatus* or *Escherichia coli.*—*Infect. Immun.* 67:2969-2974.

Roos et al. 2000—*Lactobacillus mucosae* sp. nov., a new species with in vitro mucus-binding activity isolated from pig intestine—*Int. J. Syst. Evol. Microbiol.* 50:251-258.

Scharek et al. 2000—*Bifidobacterium adolescentis* Modulates the Specific Immune Response to Another Human Gut Bacterium, *Bacteroides thetaiotaomicron*, in Gnotobiotic Rats—*Immunobiology* 5:429-441.

Scheiffele and Fuss 2002—Induction of TNBS colitis in mice—Curr. Protocols Immunol. doi: 10.1002/0471142735.im1519s49.

Schleifer et al. 1984—Transfer of *Streptococcus faecalis* and *Streptococcus faecium* to the Genus *Enterococcus* nom. rev. as *Enterococcus faecalis* comb. nov. and *Enterococcus faecium* comb. nov.—*Int. J. Syst. Evol. Microbiol.* 34:31-34.

Schwiertz et al. 2002—*Anaerostipes caccae* gen. nov., sp. nov., a new saccharolytic, acetate-utilising, butyrate-producing bacterium from human faeces—*Syst. Appl. Microbiol.* 25:46-51.

Sekirov et al. 2008—Antibiotic-induced perturbations of the intestinal microbiota alter host susceptibility to enteric infection—*Infect. Immun.* 76:4726-36.

Van den Abbeele et al. 2010—Microbial community development in a dynamic gut model is reproducible, colon region specific, and selective for Bacteroidetes and Clostridium cluster IX—*Appl. Environ. Microbiol.* 76:5237-5246.

Van den Abbeele et al. 2013—Prebiotics, faecal transplants and microbial network units to stimulate biodiversity of the human gut microbiome—*Microb. Biotechnol.* 6:335-40.

Van Loo et al. 1999—Functional food properties of non-digestible oligosaccharides: a consensus report from the ENDO project (DGXII AIRII-CT94-1095)—*Br. J. Nutr.* 81:121-32.

Vermeiren et al. 2011—Decreased colonization of fecal Clostridium coccoides/Eubacterium rectale species from ulcerative colitis patients in an in vitro dynamic gut model with mucin environment—*FEMS Microbiol. Ecol.* 79:685-696.

Vigsnaes et al. 2013—Microbiotas from UC patients display altered metabolism and reduced ability of LAB to colonize mucus—*Sci. Rep.* 3:1110.

Walter 2008—Ecological Role of Lactobacilli in the Gastrointestinal Tract: Implications for Fundamental and Biomedical Research—*Appl. Environ. Microbiol.* 74:4985-4996.

Weisburg et al. 1991—16S ribosomal DNA amplification for phylogenetic study—*J. Bacteriol.* 173:697-703.

Willing et al. 2009—Twin studies reveal specific imbalances in the mucosa-associated microbiota of patients with ileal Crohn's disease—*Inflamm. Bowel Dis.* 15:653-60.

WO 2013/037068—Method for treatment of disorders of the gastrointestinal system (Allen-Vercoe and Petrof, 2013).

WO 2014/145958A2—Network-based microbial compositions and methods (Henn et al. 2014).

---

What is claimed is:

1. A method for reduction of symptoms associated with a gastro-intestinal disorder, comprising:
orally administering to a subject having the gastro-intestinal disorder, a pharmaceutical composition comprising a functional microbial network, wherein the functional microbial network comprises an effective amount of bacterial species isolated from one or more samples and co-cultured for at least 1 day, wherein when the functional microbial network is cultured in vitro it produces a higher amount of butyrate relative to an amount of both propionate and acetate together compared to a composition comprising the bacterial species cultured in vitro which have not been co-cultured to form the functional microbial network, wherein relative amounts of butyrate, acetate, and propionate are determined based on molar percentage, and wherein the bacterial species comprise at least three of the following: *Lactobacillus plantarum, Anaerostipes caccae, Faecalibacterium prausnitzii, Butyricicoccus pullicaecorum, Roseburia inulinivorans, Akkermansia muciniphila,* or *Roseburia hominis.*

2. The method of claim 1, wherein the functional microbial network comprises bacterial species co-cultured for at least 3 days to form the functional microbial network.

3. The method of claim 1, wherein the functional microbial network comprises bacterial species co-cultured for 1 to 15 days to form the functional microbial network.

4. The method of claim 1, wherein the functional microbial network comprises bacterial species isolated from one or more fecal samples.

5. The method of claim 1, wherein the functional microbial network comprises up to 14 bacterial species.

6. The method of claim 1, wherein the bacterial species comprise the following: *Lactobacillus plantarum, Anaerostipes caccae, Faecalibacteriumprausnitzii, Butyricicoccus pullicaecorum, Roseburia inulinivorans, Akkermansia muciniphila,* and *Roseburia hominis.*

7. The method of claim 1, wherein the functional microbial network comprises at least 10^5 colony-forming units of bacteria.

8. The method of claim 1, wherein the functional microbial network comprises 10^5 to 10^11 colony-forming units of bacteria.

9. The method of claim 1, wherein the gastro-intestinal disorder is diarrhea, constipation, irritable bowel syndrome, inflammatory bowel disease, Crohn's disease, ulcerative colitis, coeliac disease, pouchitis, mucositis, or an infection of the gut.

10. The method of claim 1, wherein the symptoms associated with the gastro-intestinal disorder comprise nausea and vomiting, abdominal pain, distension, or diarrhea.

11. The method of claim 1, wherein the functional microbial network comprises bacterial species co-cultured under anaerobic conditions to form the functional microbial network.

12. A method for reduction of inflammation associated with a gastro-intestinal tract, comprising:

orally administering to a subject having said inflammation, a pharmaceutical composition comprising a functional microbial network, wherein the functional microbial network comprises an effective amount of bacterial species isolated from one or more samples and co-cultured for at least 1 day, wherein when the functional microbial network is cultured in vitro it produces a higher amount of butyrate relative to an amount of both propionate and acetate together compared to a composition comprising the bacterial species cultured in vitro which have not been co-cultured to form the functional microbial network, wherein relative amounts of butyrate, acetate, and propionate are determined based on molar percentage, and wherein the bacterial species comprise at least three of the following: *Lactobacillus plantarum, Anaerostipes caccae, Faecalibacterium prausnitzii, Butyricicoccus pullicaecorum, Roseburia inulinivorans,Akkermansia muciniphila,* or *Roseburia hominis.*

13. The method of claim 12, wherein the functional microbial network comprises bacterial species co-cultured for at least 3 days to form the functional microbial network.

14. The method of claim 12, wherein the functional microbial network comprises bacterial species co-cultured for 1 to 15 days to form the functional microbial network.

15. The method of claim 12, wherein the functional microbial network comprises bacterial species isolated from one or more fecal samples.

16. The method of claim 12, wherein the functional microbial network comprises up to 14 bacterial species.

17. The method of claim 12, wherein the bacterial species comprise the following: *Lactobacillus plantarum, Anaerostipes caccae, Faecalibacteriumprausnitzii, Butyricicoccus pullicaecorum, Roseburia inulinivorans, Akkermansia muciniphila,* and *Roseburia hominis.*

18. The method of claim 12, wherein the functional microbial network comprises at least 10^5 colony-forming units of bacteria.

19. The method of claim 12, wherein the functional microbial network comprises 10^5 to $10^1$\11 colony-forming units of bacteria.

20. The method of claim 12, wherein the inflammation is intestinal inflammation.

21. The method of claim 12, wherein the pharmaceutical composition is administered in an amount sufficient to reduce a Disease Activity Index value of the subject.

22. The method of claim 12, wherein the functional microbial network comprises bacterial species co-cultured under anaerobic conditions to form the functional microbial network.

* * * * *